United States Patent
Sameshima

(10) Patent No.: US 9,239,299 B2
(45) Date of Patent: Jan. 19, 2016

(54) PHOTOINDUCED CARRIER LIFETIME MEASURING METHOD, LIGHT INCIDENCE EFFICIENCY MEASURING METHOD, PHOTOINDUCED CARRIER LIFETIME MEASURING DEVICE, AND LIGHT INCIDENCE EFFICIENCY MEASURING DEVICE

(75) Inventor: Toshiyuki Sameshima, Fuchu (JP)

(73) Assignee: National University Corporation Tokyo University of Agriculture and Technology, Fuchu-shi (JP)

( * ) Notice: Subject to any disclaimer, the term of this patent is extended or adjusted under 35 U.S.C. 154(b) by 684 days.

(21) Appl. No.: 13/579,043

(22) PCT Filed: Sep. 6, 2010

(86) PCT No.: PCT/JP2010/065227
§ 371 (c)(1),
(2), (4) Date: Aug. 15, 2012

(87) PCT Pub. No.: WO2011/099191
PCT Pub. Date: Aug. 18, 2011

(65) Prior Publication Data
US 2012/0310556 A1  Dec. 6, 2012

(30) Foreign Application Priority Data
Feb. 15, 2010  (JP) .................... 2010-030658

(51) Int. Cl.
*G01R 15/00* (2006.01)
*G01N 22/00* (2006.01)
(Continued)

(52) U.S. Cl.
CPC ............ *G01N 22/00* (2013.01); *H01L 22/12* (2013.01); *G01R 31/2648* (2013.01); *G01R 31/2831* (2013.01)

(58) Field of Classification Search
USPC .......................................... 702/58
See application file for complete search history.

(56) References Cited

U.S. PATENT DOCUMENTS 4,809,196 A * 2/1989 Miller ................ 436/4
4,949,034 A * 8/1990 Imura et al. ......... 324/754.08
(Continued)

FOREIGN PATENT DOCUMENTS

JP      59 55013       3/1984
JP      2007 27288     2/2007

OTHER PUBLICATIONS

Sameshima, T., et al., "Analysis of Microwave Absorption Caused by Free Carriers in Silicon," Japanese Journal of Applied Physics, vol. 48, No. 2, pp. 021204.1-021204.6, (2009).

(Continued)

*Primary Examiner* — Paul D Lee
(74) *Attorney, Agent, or Firm* — Oblon, McClelland, Maier & Neustadt, L.L.P.

(57) ABSTRACT

A photoinduced carrier lifetime measuring method capable of obtaining photoinduced carrier effective lifetime of a semiconductor substrate with high accuracy regardless of the surface state of the sample. The method includes: irradiating a microwave onto a semiconductor substrate while periodically pulse-irradiating a light onto the semiconductor substrate; detecting the microwave transmitted through the semiconductor substrate or reflected by the semiconductor substrate; and obtaining the effective lifetime of photoinduced carriers generated in the semiconductor substrate by the pulse irradiation of the light, based on an irradiation duration T1 and a non-irradiation duration T2 when performing the light pulse irradiation and an integrated value of each microwave intensity obtained by the detection.

11 Claims, 8 Drawing Sheets

(51) Int. Cl.
*H01L 21/66* (2006.01)
*G01R 31/26* (2014.01)
*G01R 31/28* (2006.01)

(56) References Cited

U.S. PATENT DOCUMENTS

| | | | | |
|---|---|---|---|---|
| 5,153,503 A | * | 10/1992 | Yahata | 324/754.23 |
| 5,406,214 A | * | 4/1995 | Boda et al. | 324/750.14 |
| 5,430,386 A | * | 7/1995 | Morin et al. | 324/754.23 |
| 5,760,597 A | * | 6/1998 | Yoshida et al. | 324/754.23 |
| 2010/0188094 A1 | * | 7/2010 | Allibert et al. | 324/501 |

OTHER PUBLICATIONS

Sumie, S., et al., "Detection of Heavy Metal Contamination in Semiconductor Processes Using a Carrier Lifetime Measurement System," Kobe Steel Engineering Reports, vol. 52, No. 2, pp. 87-93, (Sep. 2002) (with partial English translation).

Borodovskii, P.A., et al., "Determination of the Minority-Carrier Lifetime in Silicon Ingots by Photoconductivity Relaxation Measured at Microwave Frequencies," Semiconductors, vol. 38, No. 9, pp. 1005-1011, (2004).

Borrego, J.M., et al., "Non-Destructive Lifetime Measurement in Silicon Wafers by Microwave Reflection," Solid-State Electronics, vol. 30, No. 2, pp. 195-203, (1987).

Kousik, G.S., et al., "Nondestructive technique to measure bulk lifetime and surface recombination velocities at the two surfaces by ifrared absorption due to pulsed optical excitation," Journal of Applied Physics, vol. 72, No. 1, p. 141, (Jul. 1992).

Sinton, R.A., et al., "Contactless determination of current-voltage characteristics and minority-carrier lifetimes in semiconductors from quasi-steady-state photoconductance data," Applied Physics Letters, vol. 69, No. 17, pp. 2510-2512, (Oct. 21, 1996).

International Search Report Issued Oct. 26, 2010 in PCT/JP10/65227 Filed Sep. 6, 2010.

* cited by examiner $\tau_b = 1 \times 10^{-5} \sim 1 \times 10^{-3}$ s
Stop = 0 cm/s
Srear = 0 cm/s $\tau_b = 1$ s
Stop = 0 cm/s
Srear = 5200~52 cm/s $\tau_b = 1$ s
Stop = 5200~52 cm/s
Srear = 0 cm/s $\tau_b = 1$ s
Stop = Srear
     = 2600~26 cm/s

PHOTOINDUCED CARRIER LIFETIME MEASURING METHOD, LIGHT INCIDENCE EFFICIENCY MEASURING METHOD, PHOTOINDUCED CARRIER LIFETIME MEASURING DEVICE, AND LIGHT INCIDENCE EFFICIENCY MEASURING DEVICE

TECHNICAL FIELD

The present invention relates to a photoinduced carrier lifetime measuring method for measuring effective lifetime of photoinduced carriers generated in a semiconductor substrate by light irradiation, and a photoinduced carrier lifetime measuring device for performing the measuring method. The present invention further relates to a light incidence efficiency measuring method for obtaining light incidence efficiency of the semiconductor substrate based on the effective lifetime, and a light incidence efficiency measuring device for performing the measuring method.

BACKGROUND ART

The photoinduced carrier lifetime is used as one of indicators for evaluating internal defects within the semiconductor substrate. The term "photoinduced carrier lifetime" means the lifetime of the photoinduced carriers (i.e., the minority carriers) generated in the semiconductor substrate by light irradiation.

A μ-PCD (microwave photoconductive decay) method (see, for example, Non-patent document 1) is known as a first example of a method and device for measuring the photoinduced carrier lifetime. In such a method, a laser is pulse-irradiated onto a semiconductor substrate for extremely short time in a state where a microwave is irradiated onto the semiconductor substrate. At this time, the reflectivity of the microwave irradiated onto the semiconductor substrate changes depending on the density of the carriers induced by the laser pulse. Thus, the effective lifetime of the photoinduced carriers of the semiconductor substrate (referred to as "effective lifetime" hereinafter) can be obtained by measuring the change of the reflectivity with time.

A QSSPC (quasi steady state photoconductivity) method (see, for example, Non-patent document 2) is known as a second example of the method and device for measuring the photoinduced carrier lifetime of a semiconductor substrate. In such a method, an inductance coil is disposed to face a semiconductor substrate, to emit RF frequency radiation. Further, a light is pulse-irradiated onto the semiconductor substrate for extremely short time. At this time, an electromagnetic wave of a RF frequency is reflected by the carriers induced by the light pulse. The photoinduced carrier effective lifetime of the semiconductor substrate can be obtained by measuring the change of the reflected wave with time as the change of the currency flowing through the coil.

Further, a microwave optical interference absorption method (see, for example, Non-patent document 3) is known as a third example of the method and device for measuring the photoinduced carrier lifetime of a semiconductor substrate. In such a method, a microwave interferometer formed of a waveguide is inserted into a semiconductor substrate, and continuous light is irradiated onto the semiconductor substrate in a state where a microwave is irradiated onto the semiconductor substrate. At this time, since the microwave is absorbed by the carriers induced by the irradiation of the continuous light, the photoinduced carrier effective lifetime can be obtained by measuring the reduction of the microwave transmittance.

PRIOR ART DOCUMENTS

Non-Patent Documents

[Non-patent document 1] J. M. Borrego, R. J. Gutmann, N. Jensen, and O. Paz: Solid-State Electronics. 30 (1987) 195.
[Non-patent document 2] J. G. S. Kousik, Z. G. Ling, and P. K. Ajmera: J. App. Phys. 72 (1992) 141.
[Non-patent document 3] T. Sameshima, H. Hayasaka, and T. Hara, Jpn. J. Appl. Phys. 48 (2009) 021204-1-6.

DISCLOSURE OF THE INVENTION

Problems to be Solved by the Invention

The μ-PCD method of the first example and the QSSPC method of the second example are methods in which strong light pulse is irradiated onto the semiconductor substrate to generate photoinduced carriers (such as electrons, holes and the like) in the semiconductor substrate, and time decay-rate of the generated photoinduced carriers is measured. These methods are widely used because of their simplicity.

However, in these methods, the decay of the photoinduced carriers generated by one light pulse is measured as the change of the reflectivity of the microwave or electromagnetic wave with time, and therefore it is necessary to generate high-density photoinduced carriers in order to maintain high measurement accuracy. Thus, it is difficult to obtain the effective lifetime in the case where the density of the photoinduced carriers is low.

With the measuring system developed for performing the aforesaid methods, it is not possible to identify the incidence rate of the microwave or RF electric field incident onto the sample, and it is not possible to analyze absorption of the microwave or absorption of the RF electric field caused by the carriers generated in the sample. Therefore, it is not possible to calculate the carrier density based on the measured signal. Thus, it is not possible to obtain the effective lifetime with high accuracy.

On the other hand, the microwave optical interference absorption method as the third example is a method adapted to measure the change of the microwave transmittance caused by the photoinduced carriers generated by irradiating continuous light onto the semiconductor substrate, wherein the microwave transmittance depends on the carrier density. Thus, it is possible to detect the photoinduced carriers having a low-density of about $1 \times 10^{11}$ cm$^{-2}$.

In other words, if the carrier density of the photoinduced carriers obtained based on the measured microwave transmittance is n, then the effective lifetime $\tau_{eff}$ can be obtained by the following Equation (1) where incident light intensity is I, photon energy is hv, sample surface reflectivity is r.

$$\tau_{eff} = nh\nu/(1-r)I \qquad (1)$$

It can be known from Equation (1) that accurate measurement of the carrier density makes it possible to accurately measure the effective lifetime. Thus, it is possible to obtain a short effective lifetime of 2 μs by using the microwave optical interference absorption method.

However, as can be known from Equation (1) that, with the aforesaid microwave optical interference absorption method, the sample surface reflectivity r of the surface of the semiconductor substrate has to be obtained in advance. Thus, in the case where the sample is a semiconductor substrate having a texture structure such as a solar cell, for example, the sample surface reflectivity r can not be determined. Further, with regard to the incident light intensity I, there is arbitrariness in signal-light intensity transfer characteristic of the detector.

Therefore, it is an object of the present invention to provide a photoinduced carrier lifetime measuring method capable of obtaining the photoinduced carrier effective lifetime of a sample semiconductor substrate with high accuracy, regardless the surface state of the sample semiconductor substrate. Further, it is another object of the present invention to provide a photoinduced carrier lifetime measuring device for achieving the aforesaid measuring method. Furthermore, it is further another object of the present invention to provide a light incidence efficiency measuring method capable of obtaining the light incidence efficiency with respect to the sample based on the effective lifetime obtained by the aforesaid measuring method, and a measuring device for performing the light incidence efficiency measuring method.

Means for Solving the Problems

To achieve the aforesaid objects, a photoinduced carrier lifetime measuring method according to an aspect of the present invention includes the following steps: irradiating a microwave onto a semiconductor substrate while periodically pulse-irradiating an light onto the semiconductor substrate; detecting the microwave transmitted through the semiconductor substrate or reflected by the semiconductor substrate; and obtaining the effective lifetime of photoinduced carriers generated in the semiconductor substrate by the pulse irradiation of the light, based on an irradiation duration T1 and a non-irradiation duration T2 when pulse-irradiating the light and an integrated value of each microwave intensity obtained by the detection.

Further, a light incidence efficiency measuring method according to another aspect of the present invention is characterized in that light incidence efficiency (1-r) is obtained from the following Equation (2)

obtaining light incidence efficiency (1-r) from the following Equation (2).

[Mathematical expression 1]

$$n=(1-r)G\tau_{\mathit{eff}} \quad (2)$$

where r is surface reflectivity, n is carrier density of photoinduced carriers, and G is light intensity (energy of one photon).

With the photoinduced carrier lifetime measuring method and the light incidence efficiency measuring method according to the present invention, the microwave transmitted through the semiconductor substrate or reflected by the semiconductor substrate is detected in a state where the light is periodically pulse-irradiated onto the semiconductor substrate. Thus, even if the photoinduced carriers generated in the semiconductor substrate by the light irradiation is of low-density, a measurement result with high sensitivity can be obtained by obtaining an integrated value of the microwave intensity detected for each of plural periodical pulse irradiations. Therefore, it is possible to obtain a detection result with high sensitivity even in the case where the semiconductor substrate is irradiated by feeble light. Further, by changing the irradiation duration T1 and the non-irradiation duration T2 and periodically pulse-irradiating the light for plural times, change of the integrated value of the microwave detection intensity with respect to change of the T1, T2 can be obtained, and carrier decay-rate can be known based on this change. Thus, the photoinduced carrier effective lifetime can be obtained without requiring information such as the surface reflectivity of the semiconductor substrate to be measured and the like.

Further, a photoinduced carrier lifetime measuring device according to further another aspect of the present invention includes a light source, a microwave source, a detecting section, and a calculating section. The light source is adapted to pulse-irradiate light for generating photoinduced carriers in a sample. The microwave source is adapted to generate a microwave for being irradiated onto the sample. The detecting section is adapted to detect the microwave transmitted through or reflected by the sample. The calculating section is adapted to calculate the effective lifetime of the photoinduced carriers generated in the sample by the pulse irradiation of the light based on an irradiation duration T1 and a non-irradiation duration T2 when periodically pulse-irradiating the light for a plurality of times and an integrated value of the intensity of the microwave detected by the detecting section.

Further, it is possible to obtain the effective lifetime based on the detection result of the microwave having high sensitivity without requiring information such as the surface reflectivity of the semiconductor substrate to be measured and the like, even in the case where the sample is irradiated by feeble light. As a result, it is possible to obtain the photoinduced carrier effective lifetime with high accuracy even in the case where the sample is a semiconductor substrate having a texture structure such as a solar cell for example.

Advantages of the Invention

Further, it is possible to obtain the effective lifetime based on the detection result of the microwave having high sensitivity without requiring information such as the surface reflectivity of the semiconductor substrate to be measured and the like, even in the case where the sample is irradiated by feeble induction light. As a result, it is possible to obtain the photoinduced carrier effective lifetime with high accuracy even in the case where the sample is a semiconductor substrate having a texture structure such as a solar cell for example.

BRIEF DESCRIPTION OF DRAWINGS

FIGS. 3A, 3B and 3C are graphs for explaining a third embodiment of the present invention, wherein FIG. 3A shows an example where light is periodically irradiated from a light source, FIG. 3B shows an example where a microwave is periodically irradiated from a microwave source, and FIG. 3C shows an example of change of carrier density with time in the case where light is periodically irradiated;

FIGS. 7A, 7B and 7C are graphs for explaining the fourth embodiment of the present invention, wherein FIG. 7A shows an example where light is periodically irradiated from a light source, FIG. 7B shows an example where a microwave is irradiated from a microwave source, and FIG. 7C shows an example of change of carrier density with time in the case where light is periodically irradiated;

BEST MODES FOR CARRYING OUT THE INVENTION

Figure 1:
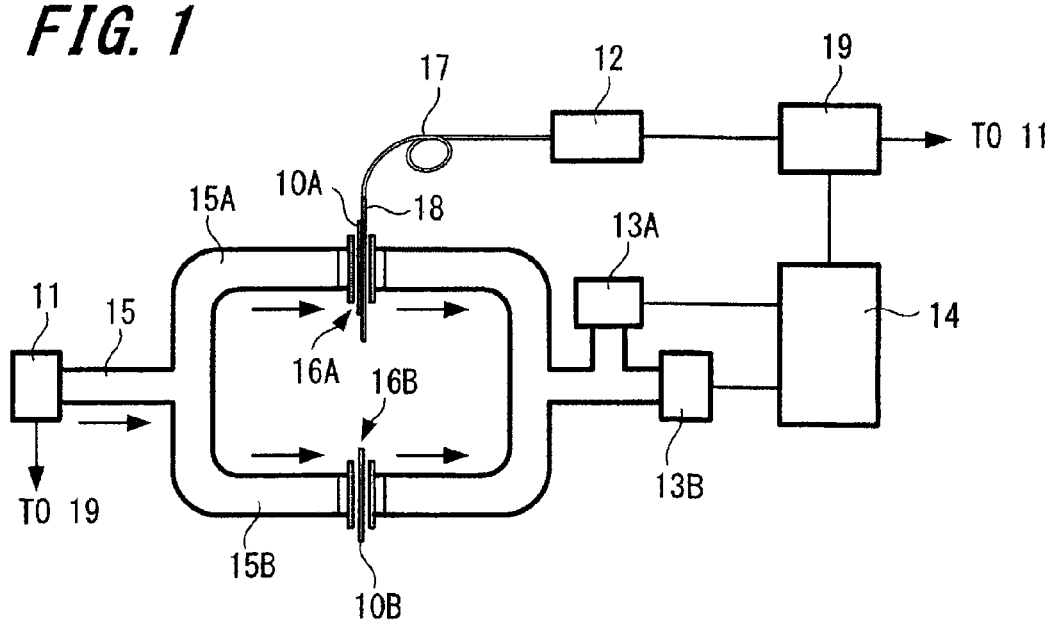
FIG. 1 is a view showing a schematic configuration of a measuring device for measuring photoinduced carrier lifetime and light incidence efficiency according to a first embodiment of the present invention.

Embodiments of the present invention will be described in the following order with reference to the attached drawings.

1. First embodiment "example of configuration of photoinduced carrier lifetime measuring device"
2. Second embodiment "modification of configuration of photoinduced carrier lifetime measuring device"
3. Third embodiment "first example of photoinduced carrier lifetime measuring method"
4. Fourth embodiment "second example of photoinduced carrier lifetime measuring method"
5. Fifth embodiment "third example of photoinduced carrier lifetime measuring method"

Incidentally, in each embodiment, like components will be denoted by like reference numerals and the explanation thereof will be omitted.

1. First Embodiment

FIG. 1 shows a schematic configuration of a photoinduced carrier lifetime measuring device and a light incidence efficiency measuring device (which are to be collectively referred to as "photoinduced carrier lifetime measuring device" hereinafter). The photoinduced carrier lifetime measuring device shown in FIG. 1 is adapted to be used to perform a photoinduced carrier lifetime measuring method and a light incidence efficiency measuring method described in the subsequent embodiments, and has the following configuration.

The photoinduced carrier lifetime measuring device includes a microwave source 11 and a light source 12, wherein the microwave source 11 is adapted to generate a microwave to be incident onto a sample semiconductor substrate 10A and a reference semiconductor substrate 10B, and the light source 12 is adapted to emit light for generating carriers in the semiconductor substrate 10A. The photoinduced carrier lifetime measuring device further includes a detecting section 13A, a detecting section 13B and a calculating section 14, wherein the detecting section 13A and the detecting section 13B are adapted to detect the intensity of the microwave transmitted through the semiconductor substrates 10A, 10B, and the calculating section 14 is adapted to calculate the photoinduced carrier lifetime and the light incidence efficiency based on the microwave intensity detected by the detecting sections 13A, 13B.

The photoinduced carrier lifetime measuring device has a waveguide 15, which constitutes a microwave interferometer, interposed between the microwave source 11 and the detecting sections 13A, 13B. The waveguide 15 is branched into two waveguides 15A, 15B in a middle portion between the microwave source 11 and the detecting sections 13A, 13B. One branched waveguide 15A is provided with a gap 16A into which the sample semiconductor substrate 10A is inserted. The other branched waveguide 15B is provided with a gap 16B into which the reference semiconductor substrate 10B is inserted. The semiconductor substrates 10A, 10B are respectively inserted into the gaps 16A, 16B in a direction substantially perpendicular to the extending direction of the waveguides 15A, 15B. The gaps 16A, 16B are disposed at symmetrical positions of the waveguides 15A, 15B.

The branched waveguides 15A, 15B are connected to each other at a position behind the gaps 16A, 16B when viewed from the microwave source 11. Further, the connected waveguide 15 is branched again, and the two branches are respectively connected to the detecting section 13A and the detecting section 13B.

Thus, in the photoinduced carrier lifetime measuring device shown in FIG. 1, the microwave generated by the microwave source 11 passes through the waveguide 15 so as to be irradiated onto the semiconductor substrate 10A, 10B inserted into the gaps 16A, 16B of the waveguides 15A, 15B. Further, the microwave transmitted through the semiconductor substrate 10A, 10B passes through the waveguides 15A, 15B so as to be guided to the detecting sections 13A, 13B respectively.

In the aforesaid configuration, a light-guiding plate 18 for causing the light from the light source 12 to be incident onto the semiconductor substrate 10A is inserted into the gap 16A into which the sample semiconductor substrate 10A is inserted. The light-guiding plate 18 is inserted at a position closer to the side of the detecting sections 13A, 13B (or the side of the microwave source 11) than the position at which the semiconductor substrate 10A is inserted, so that the light-guiding plate 18 abuts the semiconductor substrate 10A inserted into the gap 16A. The light-guiding plate 18 is connected to the light source 12 through an optical fiber 17. Incidentally, the light-guiding plate 18 may also be provided at two positions where the semiconductor substrate 10A is inserted, both on the side of the detecting sections 13A, 13B and on the side of the microwave source 11.

Here, the microwave source 11 generates the microwave in synchronization with the light irradiation from the light source 12.

The light source 12 is adapted to periodically pulse-irradiate light onto the sample semiconductor substrate 10A so as to generate carriers in the semiconductor substrate. The light source 12 may be configured by a YAG (yttrium aluminum garnet) laser, for example. Note that the light source 12 is not limited to the YAG laser, but may also be any other light source (such as a light-emitting diode (LED), a xenon lamp, a halogen lamp and the like) as long as the light emitted by the light source has a wavelength possible to be absorbed by the semiconductor substrate, particularly has a wavelength ranging from 250 nm to 2500 nm. Further, the period of the pulse irradiation of the light of the light source 12 can be changed to any different period where irradiation duration T1=non-irradiation duration T2. For example, the irradiation duration T1 and the non-irradiation duration T2 may be arbitrarily changed in a range from 0.01 ms to 0.1 s.

The detecting section 13A detects a difference $I_{A-B}$ between a microwave transmission intensity $J_A$ of the microwave transmitted through the sample semiconductor substrate 10A and a microwave transmission intensity $J_B$ of the microwave transmitted through the reference semiconductor substrate 10B. Further, the detecting section 13B detects a sum $I_{A+B}$, of the microwave transmission intensity $J_A$ of the microwave transmitted through the sample semiconductor substrate 10A and the microwave transmission intensity $J_B$ of the microwave transmitted through the reference semiconductor substrate 10B. In the photoinduced carrier lifetime measuring device shown in FIG. 1, the microwave transmission intensity is detected and amplified by detecting the sum $J_{A+B}$ of and the difference $J_{A-B}$ between the microwave transmission intensity $J_A$ and the microwave transmission intensity $J_B$, and therefore the detection sensitivity of the microwave can be improved.

Based on the microwave transmission intensity detected by the detecting section 13A, 13B and the period of the light emitted from the light source 12, the calculating section 14 calculates the photoinduced carrier lifetime and light incidence efficiency of the semiconductor substrate 10A inserted into the gap 16A. For example, in the calculating section 14, first the carrier density of the photoinduced carriers generated in the semiconductor substrate 10A by the periodical light irradiation is obtained by using a method such as the method described in Non-patent document 3. Then, the photoinduced carrier effective lifetime and the effective light incidence efficiency are obtained based on the obtained carrier density. The calculation steps of the effective lifetime and the effective light incidence efficiency in the calculating section 14 will be described later in more detail when describing the photoinduced carrier lifetime measuring method.

Incidentally, the measuring device shown in FIG. 1 may also be provided with a controller 19 for controlling the irradiation of the microwave irradiated from the microwave source 11 and the irradiation of the light irradiated from the light source 12, based on the result calculated by the calculating section 14.

Further, although not shown in the drawings, the measuring device shown in FIG. 1 may also be provided with a position aligning section for selectively irradiating the microwave generated by the microwave source onto each of a plurality of areas of the sample semiconductor substrate 10A, wherein the plurality of areas are obtained by dividing a principal surface of the sample semiconductor substrate 10A. For example, a movable stage that can move the semiconductor substrate 10A inserted into the gap 16A in a direction perpendicular to the incident direction of the microwave may be used as the position aligning section. Further, instead of the movable stage, a microwave scanning section that can move the incident position of the microwave with respect to the semiconductor substrate 10A inserted into the gap 16A may be used.

Note that the measuring device shown in FIG. 1 is merely an example of the photoinduced carrier lifetime and light incidence efficiency measuring device, and it is also possible to configure the photoinduced carrier lifetime and light incidence efficiency measuring device in other ways different from the aforesaid configuration.

For example, in the measuring device shown in FIG. 1, the waveguide 15 is branched into two waveguides, and the microwave transmittance is accurately obtained by using the sum of the microwave transmittance of the sample semiconductor substrate 10A and the microwave transmittance of the reference semiconductor substrate 10B, and the difference between the microwave transmittance of the sample semiconductor substrate 10A and the microwave transmittance of the reference semiconductor substrate 10B; however, the photoinduced carrier lifetime measuring device may also have a configuration in which the waveguide 15B and the detecting section 13B are eliminated.

In such a case, in photoinduced carrier lifetime measuring device includes a microwave source 11 that generates the microwave, a light source 12 that irradiates light onto a semiconductor substrate 10A so as to generate carriers, a detecting section 13A, a calculating section 14, and a waveguide 15 with no branch. The waveguide 15 is provided with a gap into which the sample semiconductor substrate 10A is inserted. A light-guiding plate 18 connected to the light source 12 by an optical fiber 17 is inserted into the gap. In such a measuring device, the microwave source 11 and the light source 12 have the same configurations as those in the measuring device of the first embodiment. The detecting section 13A detects the microwave transmission intensity $J_A$ of the microwave transmitted through the sample semiconductor substrate 10A. Based on the microwave transmission intensity $J_A$ detected by the detecting section 13A, the calculating section 14 calculates the carrier density, the effective lifetime and the effective light incidence efficiency of the photoinduction in the semiconductor substrate 10A.

The photoinduced carrier lifetime measuring device according to the first embodiment can be used to perform the photoinduced carrier lifetime measuring method and the light incidence efficiency measuring method (which are to be described later).

2. Second Embodiment

Figure 2:
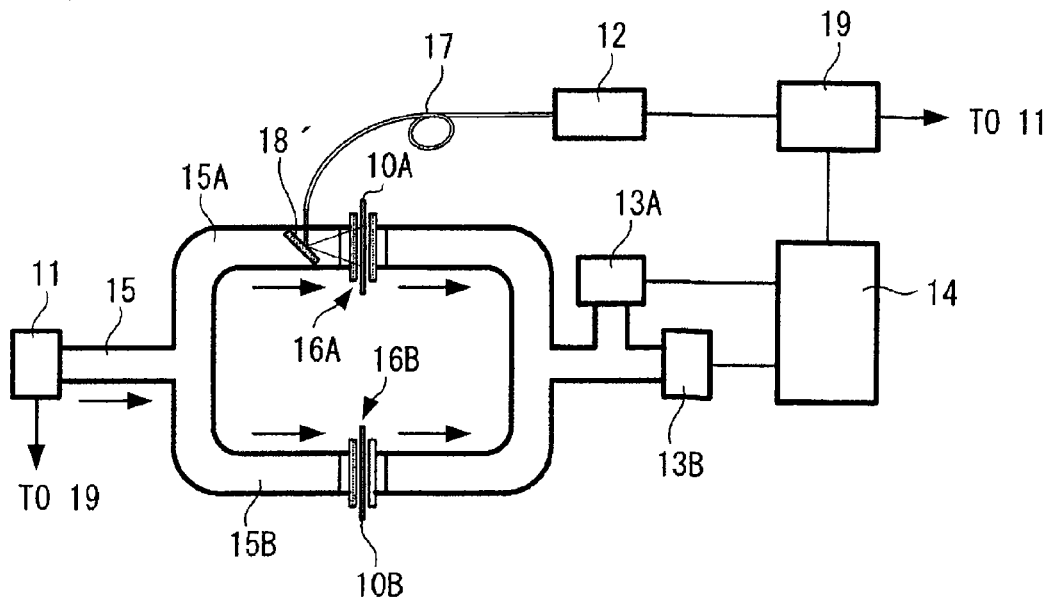
FIG. 2 is a view showing a schematic configuration of a measuring device for measuring photoinduced carrier lifetime and light incidence efficiency according to a second embodiment of the present invention.

FIG. 2 shows a schematic configuration of a modification of the photoinduced carrier lifetime measuring device and the light incidence efficiency measuring device (collectively referred to as a "photoinduced carrier lifetime measuring device" hereinafter). The photoinduced carrier lifetime measuring device shown in FIG. 2 is identical to the photoinduced carrier lifetime measuring device shown in FIG. 1 except that, instead of the light-guiding plate 18 shown in FIG. 1, a diffusion reflection plate 18' is provided.

That is, in the photoinduced carrier lifetime measuring device shown in FIG. 2, a small hole is formed in the side wall of the waveguide 15A. An end portion of the optical fiber 17 connected the light source 12 is attached to the hole, and the light from the light source 12 is guided to the waveguide 15A through the optical fiber 17. The diffusion reflection plate 18' is arranged inside the waveguide 15A. The diffusion reflection plate 18' reflects the light from the optical fiber 17 to the side of the gap 16A into which the semiconductor substrate 10A is inserted, while diffusing the light. Further, the microwave generated by the microwave source 11 is transmitted through the diffusion reflection plate 18'. The diffusion reflection plate 18' is formed of a fluororesin, for example.

In the waveguide 15A, the diffusion reflection plate 18' and the optical fiber 17 connected to the diffusion reflection plate 18' are arranged at least on one of both the side of the microwave source 11 and the side of the detecting sections 13A, 13B of the gap 16A into which the sample semiconductor substrate 10A is inserted.

Similar to the measuring device of the first embodiment shown in FIG. 1, the measuring device of the second embodiment shown in FIG. 2 may also be provided with a movable stage that that can move the semiconductor substrate 10A inserted into the gap 16A in a direction perpendicular to the incident direction of the microwave. Further, instead of the movable stage, a microwave scanning section that can move the incident position of the microwave with respect to the semiconductor substrate 10A inserted into the gap 16A may be provided.

Further, similar to the measuring device of the first embodiment shown in FIG. 1, the waveguide 15B and the detecting section 13B in the measuring device of the second embodiment may also be eliminated.

Similar to the measuring device of the first embodiment, the photoinduced carrier lifetime measuring device according to the second embodiment may also be used to perform the photoinduced carrier lifetime measuring method and the light incidence efficiency measuring method (which are to be described later).

3. Third Embodiment

Next, a first example of the photoinduced carrier lifetime measuring method will be described below. The photoinduced carrier effective lifetime measuring method and the effective light incidence efficiency measuring method will be described below by using the photoinduced carrier lifetime measuring device shown in FIG. 1 or FIG. 2.

<Photoinduced Carrier Lifetime Measuring Method>

First, a data table to be used in the photoinduced carrier lifetime measuring method is previously created as follows.

Figure 3A:
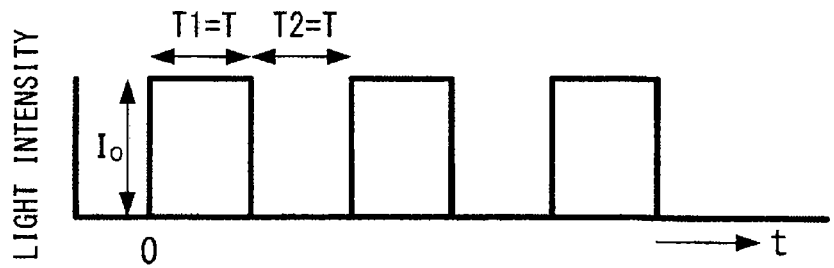

First, irradiation condition of the light for generating the carriers in the sample semiconductor substrate 10A is set. Here, as shown in FIG. 3A for example, light having an intensity of $I_0$ is intermittently pulse-irradiated from the light source 12 with a predetermined period. In such periodical pulse irradiation of the light, the irradiation duration of the light (i.e., the pulse width) is defined as "irradiation duration T1", and the non-irradiation duration of the light (i.e., the pulse interval) is defined as "non-irradiation duration T2". It is preferred that both the irradiation duration T1 and the non-irradiation duration T2 are set in a time range that covers the value of the photoinduced carrier (minority carrier) effective lifetime of the semiconductor. Generally, the effective lifetime of a silicon film and a silicon substrate is in a range from 1 μs to 0.01 s. Thus, it is preferred that the time range of the irradiation duration T1 and the non-irradiation duration T2 is the range from 1 μs to 0.01 s. Here, the irradiation duration T1 and the non-irradiation duration T2 are set so that irradiation duration T1=non-irradiation duration T2 (i.e., T1=T2).

Figure 3B:
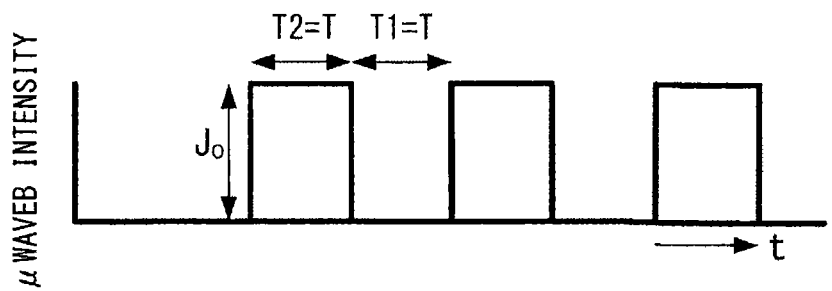

Further, generation condition of the microwave (which is the measuring light) is set. Here, as shown in FIG. 3B for example, the microwave is periodically incident onto the semiconductor substrate from the microwave source 11 at an intensity of $I_0$ in synchronization with the pulse irradiation of the light. At this time, the irradiation duration T1 of the light and the non-irradiation duration of the microwave are not superimposed on each other. In other words, the microwave is not irradiated during the irradiation duration T1 of the light, and the microwave is irradiated during the non-irradiation duration T2.

In the pulse irradiation of the light set as above, the photoinduced carriers are generated in the semiconductor substrate 10A by irradiating the light; and when the light irradiation is completed, carrier density n of the induced photoinduced carriers decays with the lifetime $\tau_{eff}$. The decay can be expressed as the following Equation (3).

[Mathematical expression 2]

$$n = n_0 \frac{e^{-\frac{T_1}{\tau_{eff}}} - 1}{e^{-\frac{T_1}{\tau_{eff}}} - e^{\frac{T_2}{\tau_{eff}}}} e^{\frac{T_1+T_2}{\tau_{eff}}} e^{-\frac{t}{\tau_{eff}}} \quad (3)$$

The $n_0$ in Equation (3) represents the carrier density of the photoinduced carriers generated in the semiconductor substrate 10A in the case where the light is continuously irradiated (i.e., in the case where the light from the light source 12 is continuously irradiated, instead of being periodically pulse-irradiated as shown in FIG. 3A).

Figure 3C:
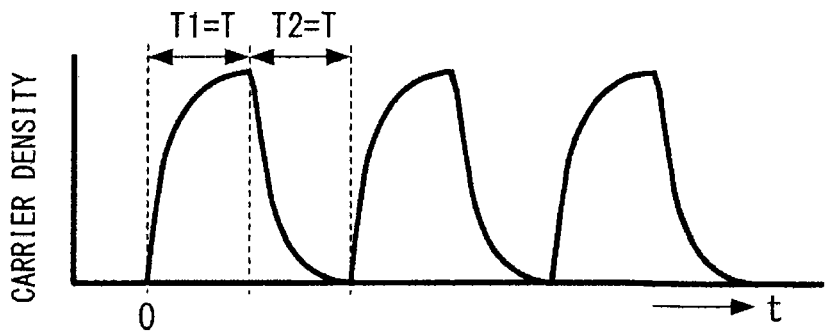

FIG. 3C shows an example of the change of the carrier density with time in the case where the light is periodically pulse-irradiated onto the semiconductor substrate 10A. As shown in FIG. 3C, in the semiconductor substrate 10A, the carrier density increases during the irradiation duration T1 of the light. Further, the carrier density decreases during the non-irradiation duration T2 while the irradiation of the light is stopped. Under the generation condition of the microwave set above, the microwave is incident onto the semiconductor substrate 10A in the time while the carrier density deceases.

In the incident microwave incident onto the semiconductor substrate 10A, the microwave intensity of the microwave transmitted through the semiconductor substrate 10A is detected, the microwave transmittance is calculated based on the detected microwave intensity, and the calculated microwave transmittance is integrated. The integrated value obtained by performing the integration is a value corresponding to the average value of the carrier density n in the non-irradiation duration T2. The average value of the carrier density n in the non-irradiation duration T2 is expressed as the following Equation (4).

[Mathematical expression 3]

$$\bar{n} = \frac{1}{T_2} \int_{T_1}^{T_1+T_2} n \, dt = \frac{n_0 \tau_{eff}}{T_2} \frac{\left(e^{-\frac{T_1}{\tau_{eff}}} - 1\right)\left(e^{\frac{T_2}{\tau_{eff}}} - 1\right)}{e^{-\frac{T_1}{\tau_{eff}}} - e^{\frac{T_2}{\tau_{eff}}}} \quad (4)$$

It can be known from Equation (4) that the integrated average value (the integrated value) of the carrier density n depends on the irradiation duration T1, the non-irradiation duration T2, the photoinduced carrier effective lifetime $\tau_{eff}$, and the carrier density $n_0$ when continuously performing light irradiation.

Here, in the case where the irradiation duration T1 is equal to the non-irradiation duration T2 (i.e., T1=T2) in Equation (4), the average value of the carrier density n is expressed as the following Equation (5).

[Mathematical expression 4]

$$<n> = \frac{n_0 \tau_{eff}}{T_1} \frac{\left(e^{-\frac{T_1}{\tau_{eff}}} - 1\right)\left(e^{\frac{T_1}{\tau_{eff}}} - 1\right)}{e^{-\frac{T_1}{\tau_{eff}}} - e^{\frac{T_1}{\tau_{eff}}}} \quad (5)$$

The data table is created by using Equation (5). Here, several different effective lifetimes $\tau_{eff}$ are set, and the variation of the average value <n> of the carrier density resulted from the variation of the irradiation duration T1 (=non-irradiation duration T2) is calculated by using Equation (5). Further, the ratio <n>/$n_0$ of the average value <n> of the carrier density to the carrier density $n_0$ when continuously performing light irradiation is calculated for each effective lifetime $\tau_{eff}$, and the ratio <n>/$n_0$ is plotted with respect to the irradiation duration T1. Thus, a data table shown in FIG. 4 is obtained.

Figure 4:
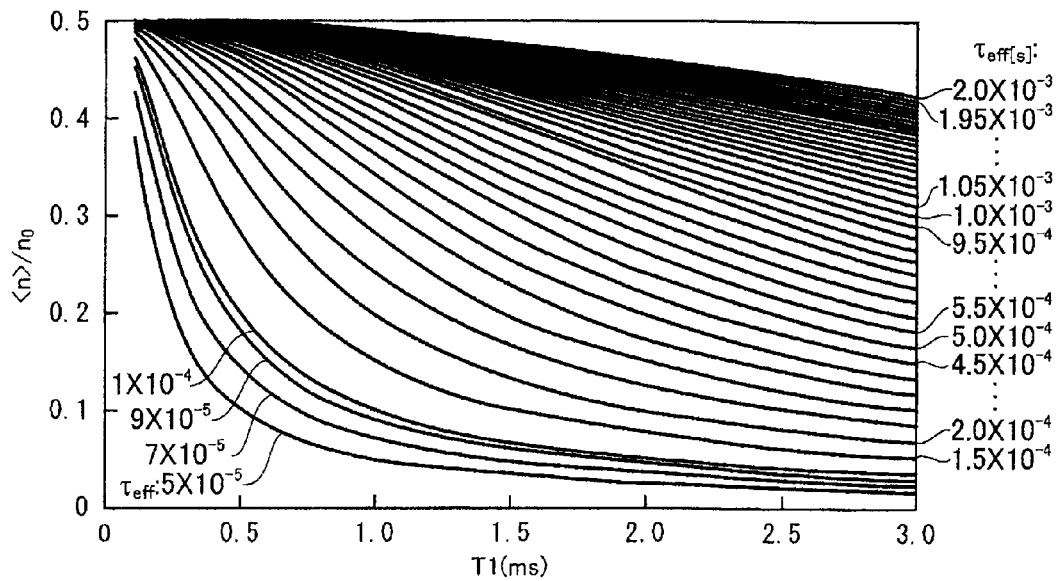
FIG. 4 is a graph showing the relation between carrier density ratio <n>/$n_0$ calculated using Equation (5) for each effective lifetime $\tau_{\mathit{eff}}$ and T1.

In other words, the data table shown in FIG. 4 shows the relation between <n>/$n_0$ and the irradiation duration T1 (=non-irradiation duration T2) for each photoinduced carrier effective lifetime $\tau_{eff}$. In FIG. 4, the vertical axis represents the ratio $<n>/n_0$ of the carrier density $<n>$ based on the microwave transmission intensity detected in the non-irradiation duration T2 to the carrier density $n_0$ when continuously performing light irradiation. The horizontal axis represents the irradiation duration T1 (ms) (=non-irradiation duration T2). In FIG. 4, the effective lifetimes $\tau_{eff}$ are set from $5\times10^{-4}$ (s) to $2.0\times10^{-3}$ (s) at an interval of $0.5\times10^{-4}$ (s). Further, the ratio $<n>/n_0$ of the carrier density $<n>$ to the carrier density $n_0$ is calculated using the aforesaid Equation (5) for each photoinduced carrier effective lifetime $\tau_{eff}$ by changing the irradiation duration T1 (=non-irradiation duration T2) from 0 ms to 3 ms, and the results are plotted into graph.

As shown in FIG. 4, the maximum of $<n>/n_0$ is 0.5 times the carrier density $n_0$ when continuously performing light irradiation. Further, $<n>/n_0$ plots regular curves with respect to both the lifetime $\tau_{eff}$ and the T1.

Next, by using the data table of FIG. 4, the relation between $<n>/n_0$ and T1 is obtained for a sample whose photoinduced carrier effective lifetime is unknown, and then the obtained the relation between $<n>/n_0$ and T1 is compared with the curve of each effective lifetime $\tau_{eff}$ shown in FIG. 4 to thereby obtain the effective lifetime of the sample.

To be specific, first, the sample semiconductor substrate 10A is inserted into the gap 16A of the waveguide 15A of the photoinduced carrier lifetime measuring device shown in FIG. 1 or FIG. 2. At this time, the light-guiding plate 18 is disposed so as to abut the irradiation surface of the light of the semiconductor substrate 10A, or the semiconductor substrate 10A is disposed so that the irradiation surface of the light of the semiconductor substrate 10A faces the diffusion reflection plate 18'. Further, the semiconductor substrates 10A, 10B are disposed so that they have the same direction with respect to the microwave source 11.

Next, the light is periodically pulse-irradiated from the light source 12 onto the semiconductor substrate 10A. The irradiation condition of the light is set as the aforesaid condition where, for example, the irradiation duration T1 is equal to the non-irradiation duration T2 as shown in FIG. 3A.

Further, the microwave is irradiated from the microwave source 11 onto the semiconductor substrates 10A, 10B in synchronization with the pulse irradiation of the light. The irradiation condition of the microwave is set as the aforesaid condition where, for example, the irradiation of the microwave has reversed phase with respect to the pulse irradiation of the light as shown in FIG. 3B; i.e., the microwave is not irradiated during the irradiation duration T1 of the light, and the microwave is irradiated during the non-irradiation duration T2.

In such a state, the microwave transmitted through the semiconductor substrates 10A, 10B is detected by the detecting sections 13A, 13B. In the calculating section 14, the microwave transmission intensity detected by the detecting section 13A, and the microwave transmission intensity detected by the detecting section 13B are summed and amplified.

Further, in the calculating section 14, the microwave transmission intensity detected in each non-irradiation duration T2 of the light is compared with the microwave transmission intensity detected in the preceding non-irradiation duration T2. Further, it is judged, at a point where the difference of the microwave transmission intensities compared has reached a predetermined value, that the change of the carrier density with time has become stable during the periodical pulse irradiation of the light, as shown in FIG. 3C.

After it is judged that the change of the carrier density has become stable, in the calculating section 14, the microwave transmittance is calculated based on the amplified microwave intensity and further, an integrated value is obtained. The integrated value is expressed as the aforesaid Equation (5), where the average value of the carrier density in a predetermined irradiation duration T1 (=non-irradiation duration T2) is $<n>$. Incidentally, the microwave transmittance of the reference semiconductor substrate 10B, for example, may be used to calculate the microwave transmittance, and the microwave transmittance of the reference semiconductor substrate 10B is obtained in advance.

Further, in the calculating section 14, the relation between $<n>/n_0$ and T1 is obtained based on the average value $<n>$ of the carrier density in a predetermined irradiation duration T1 (=non-irradiation duration T2), and the carrier density $n_0$ when continuously performing light irradiation calculated based on the measurement previously performed. Incidentally, the carrier density $n_0$ when continuously performing light irradiation can be determined by detecting the microwave transmission intensity using the measuring device shown in FIG. 1, and analyzing the decay-rate of the detected microwave transmission intensity.

Here, irradiation duration T1 (=non-irradiation duration T2) is changed by the controller 19 within a ranged set when creating the data table shown in FIG. 4.

Further, $<n>/n_0$ is calculated for each changed the irradiation duration T1 (=the non-irradiation duration T2), and the relation between $<n>/n_0$ and T1 calculated for the unknown sample is fitted to the data of the data table shown in FIG. 4, so that the effective lifetime $\tau_{eff}$ of the unknown sample is obtained.

As described above, in the photoinduced carrier lifetime measuring method according to the third embodiment, the surface reflectivity r of the sample semiconductor substrate is not included as a parameter for obtaining the photoinduced carrier effective lifetime $\tau_{eff}$. In a conventional microwave optical interference absorption method, the surface reflectivity r of the semiconductor substrate has to be obtained in advance. In contrast, in the photoinduced carrier lifetime measuring method according to the third embodiment, the photoinduced carrier effective lifetime $\tau_{eff}$ of the sample semiconductor substrate 10A can be measured without using the surface reflectivity of the semiconductor substrate.

Further, since the light is periodically pulse-irradiated onto the sample semiconductor substrate, it is possible to obtain the measurement result with high sensitivity by obtaining an integrated value of the microwave intensity detected for each of plural periodical pulse irradiations.

Thus, it is possible to obtain the photoinduced carrier effective lifetime with high sensitivity even in the case where it is difficult to measure the surface reflectivity of the semiconductor substrate, particularly in the case where the semiconductor substrate is a solar cell structure that has a texture whose reflectivity actually can not be determined. Further, it is possible to obtain the effective lifetime based on the detection result of the microwave with high sensitivity, even in the case where the semiconductor substrate is irradiated by feeble light.

<Light Incidence Efficiency Measuring Method>

Next, a light incidence efficiency measuring method for obtaining the effective light incidence efficiency of the semiconductor substrate based on the photoinduced carrier effective lifetime obtained by the aforesaid method will be described below.

First, the carrier density n of the photoinduced carriers constantly existing in the semiconductor substrate can be expressed as the following Equation (2), which has been discussed before. In Equation (2), r is effective surface reflectivity, G is intensity (i.e., energy of one photon) of the continuously irradiated light, and $\tau_{\textit{eff}}$ is the effective lifetime. Here, the effective surface reflectivity r is the actual reflectivity, which is obtained when light scattering and the like of the surface of the sample semiconductor substrate are taken into consideration, and is the reflectivity of the surface of a semiconductor substrate having a texture structure, for example.

[Mathematical Expression 5]

$$n=(1-r)G\tau_{\textit{eff}} \qquad (2)$$

In the aforesaid Equation (2), the carrier density n is a value when continuously performing light irradiation (i.e., is $n_0$), and can be determined by detecting the microwave transmission intensity using the measuring device shown in FIG. 1, and analyzing the decay-rate of the detected microwave transmission intensity. Further, the photon flux G can be determined by accurately measuring the intensity of the light irradiation. Further, the effective lifetime $\tau_{\textit{eff}}$ can be obtained by the photoinduced carrier lifetime measuring method according to the aforesaid embodiment.

Thus, it is possible to obtain effective light incidence efficiency (1-r) of the sample semiconductor substrate 10A using the aforesaid Equation (2) and based on the effective lifetime $\tau_{\textit{eff}}$ obtained by the aforesaid photoinduced carrier lifetime measuring method.

Further, the carrier density <n> of the photoinduced carriers in the case where periodical light is irradiated can be obtained by changing the average intensity of the photon flux G of Equation (2) into the following Equation (6) according to the irradiation duration T1 and the non-irradiation duration T2.

[Mathematical expression 6]

$$<n> = (1-r)\frac{GT_1}{(T_1+T_2)}\tau_{\textit{eff}} \qquad 6)$$

Thus, by using the aforesaid Equation (6), it is possible to obtain the effective light incidence efficiency (1-r) of the sample semiconductor substrate 10A based on the effective lifetime $\tau_{\textit{eff}}$ obtained by the aforesaid photoinduced carrier lifetime measuring method.

Generally, the optical reflectivity of the semiconductor substrate and the like can be optically determined using a spectrometer. However, in the case where a transparent heteroecious thin film (such as an oxide film) is formed on the surface of the semiconductor, the reflectivity will largely change according to the light incidence angle. Thus, conventionally, in order to measure the effective optical reflectivity, it is necessary to know the distribution of the light incidence angle with respect to the sample of the light source. Further, in the case where the surface of the semiconductor substrate has convexoconcaves, there is a possibility that the light might be diffuse-reflected, and a portion of the reflected light might be incident on the semiconductor substrate again. Thus, in the case where the surface of the semiconductor substrate has convexoconcaves, it will be further difficult to spectroscopically determine the effective reflectivity.

In Example 1, an n-type silicon substrate coated with a thermally-oxidized film was used as the sample semiconductor substrate, wherein the thickness of the silicon substrate was 525 μm, and the thickness of the thermally-oxidized film was 100 nm. A light having a wavelength of 532 nm was continuously irradiated onto the silicon substrate at an intensity of 20 mW/cm² to obtain the carrier density $n_0$ of the photoinduced carriers. Further, a light having a wavelength of 532 nm was periodically pulse-irradiated onto the same silicon substrate at an intensity of 20 mW/cm² to respectively obtain the carrier densities <n> of the silicon substrate while changing the irradiation duration T1 (=the non-irradiation duration T2).

Example 1

Measurement of Photoinduced Carrier Lifetime

The photoinduced carrier effective lifetime of the semiconductor substrate was obtained by using the aforesaid photoinduced carrier lifetime measuring device and applying the photoinduced carrier lifetime measuring method according to the third embodiment.

In Example 1, an n-type silicon substrate coated with a thermally-oxidized film was used as the sample semiconductor substrate, wherein the thickness of the silicon substrate was 525 μm, and the thickness of the thermally-oxidized film was 100 nm. An induction light having a wavelength of 532 nm was continuously irradiated onto the silicon substrate at an intensity of 20 mW/cm² to obtain the carrier density $n_0$ of the photoinduced carriers. Further, an induction light having a wavelength of 532 nm was periodically pulse-irradiated onto the same silicon substrate at an intensity of 20 mW/cm² to respectively obtain the carrier densities <n> of the silicon substrate while changing the irradiation duration T1 (=the non-irradiation duration T2).

Figure 5:
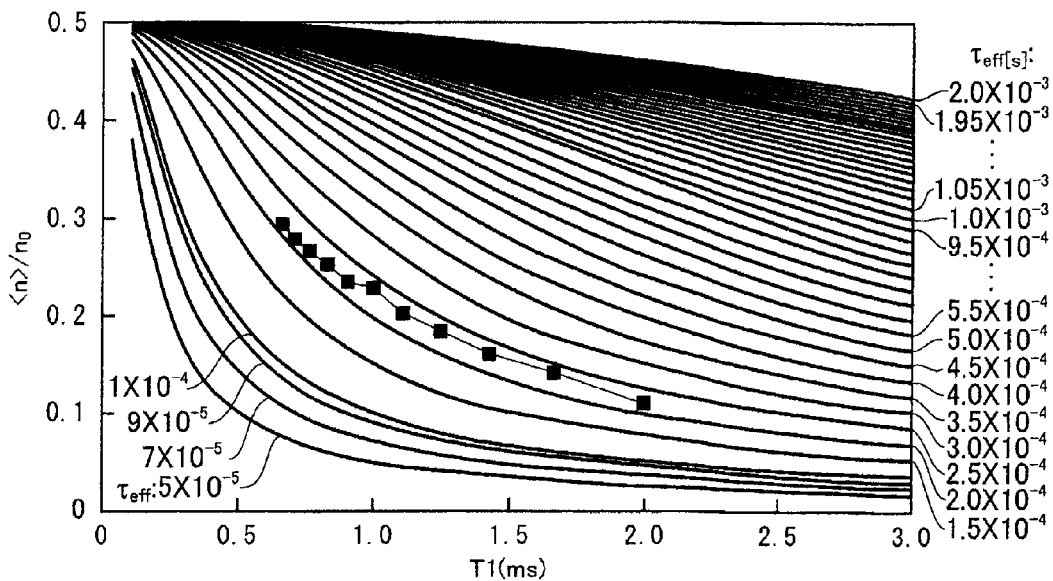
FIG. 5 is a graph showing the relation between <n>/$n_0$ and T1 in Example 1.

In FIG. 5, the relation between the ratio <n>/$n_0$ of the carrier density obtained in Example 1 and the irradiation duration T1 is indicated by mark ♦. FIG. 5 is a graph showing the relation between <n>/$n_0$ obtained in Example 1 and T1 superimposed onto the data table of the calculated values of <n>/$n_0$ and T1 of FIG. 4.

It can be known by comparing the calculated values of <n>/$n_0$ and T1 shown in FIG. 4 with the relation between <n>/$n_0$ and T1 shown in FIG. 5 that the photoinduced carrier effective lifetime $\tau_{\textit{eff}}$ of the silicon substrate used as the sample in Example 1 is approximately 2.2×10⁻⁴ (s).

Example 2

Measurement of Photoinduced Carrier Lifetime and Measurement of Light Incidence Efficiency The effective lifetime of the semiconductor substrate was obtained by using the aforesaid photoinduced carrier lifetime measuring device and applying the photoinduced carrier lifetime measuring method of the third embodiment, and further, the effective light incidence efficiency of the semiconductor substrate was obtained based on the obtained effective lifetime.

In Example 2, an n-type silicon substrate coated with a thermally-oxidized film was used as the sample semiconductor substrate, wherein the thickness of the silicon substrate is 525 μm, and the thickness of the thermally-oxidized film was 100 nm. The top surface of the silicon substrate was mirror-polished, and the rear surface of the silicon substrate was a rough surface not mirror-polished. The top surface and the rear surface of the silicon substrate were each coated with a thermally-oxidized film.

A light having a wavelength of 532 nm was continuously irradiated from a green surface light source onto the mirror top surface and the rough rear surface of the silicon substrate at an intensity of 1.8 mW/cm² to respectively obtain the carrier density $n_0$ of the mirror top surface and the carrier density $n_0$ of the rough rear surface. The carrier density when continuously irradiating the light onto the mirror top surface was $n_0=1.32\times10^{12}$ cm$^{-2}$, and the carrier density when continuously irradiating the light on the rough rear surface was $n_0=1.68\times10^{12}$ cm$^{-2}$.

Further, a light having a wavelength of 532 nm was periodically pulse-irradiated from a green surface light source onto the mirror top surface and the rough rear surface of the same silicon substrate at an intensity of 1.8 mW/cm$^2$ to respectively obtain the carrier densities <n> of the silicon substrate while changing the irradiation duration T1 (=the non-irradiation duration T2).

The relation between <n>/$n_0$ of the carrier density obtained in Example 2 and irradiation duration T1 was superimposed onto the data table shown in FIG. 4 to compare the both so as to obtain the effective lifetime $\tau_{eff}$ of the photoinduced carriers for both the case where the light was irradiated onto the mirror top surface and the case where the light was irradiated onto the rough rear surface of the semiconductor substrate. In both the case of the mirror top surface and the case of the rough rear surface, the effective lifetime $\tau_{eff}$ was approximately $4.0\times10^{-4}$ (s).

Next, the effective incidence efficiency (1−r) was calculated based on the previously calculated carrier density $n_0$ (=$1.32\times10^{12}$ cm$^{-2}$) when continuously irradiating the light onto the mirror top surface 7, the photon flux G (=$4.82\times10^{15}$ cm$^{-2}$ s$^{-1}$) obtained by performing measurement, the previously obtained effective lifetime $\tau_{eff}$ (=approximately $4.0\times10^{-4}$ (s)), and the aforesaid Equation (6). As a result, the effective light incidence efficiency with respect to the mirror top surface was: (1−r)=0.68, and the effective reflectivity was r=0.32.

Further, the effective incidence efficiency (1−r) was calculated based on the previously calculated carrier density $n_0$ (=$1.68\times10^{12}$ cm$^{-2}$) when continuously irradiating the light onto the rough rear surface, the photon flux G (=$4.82\times10^{15}$ cm$^{-2}$ s$^{-1}$) obtained by performing measurement, the previously obtained effective lifetime $\tau_{eff}$ (=approximately $4.0\times10^{-4}$ (s)), and the aforesaid Equation (6). As a result, the effective light incidence efficiency with respect to the rough rear surface was: (1−r)=0.87, and the effective reflectivity was r=0.13.

Incidentally, in the aforesaid third embodiment, the value <n>/$n_0$ of the average value <n> of the carrier density to the carrier density $n_0$ when continuously performing light irradiation is used in order to normalize the average value <n> of the carrier density in the non-irradiation duration T2 (=irradiation duration T1) obtained according to the integrated value of the microwave transmission intensity. However, the average value <n> of the carrier density may also be used as it is without being normalized. The average value <n> of the carrier density in the non-irradiation duration T2 (=irradiation duration T1) may also be normalized as a value corresponding to the average value of the carrier density in the irradiation duration T1. In such a case, the microwave transmission intensity is also measured in the irradiation duration T1.

4. Fourth Embodiment

Figure 6:
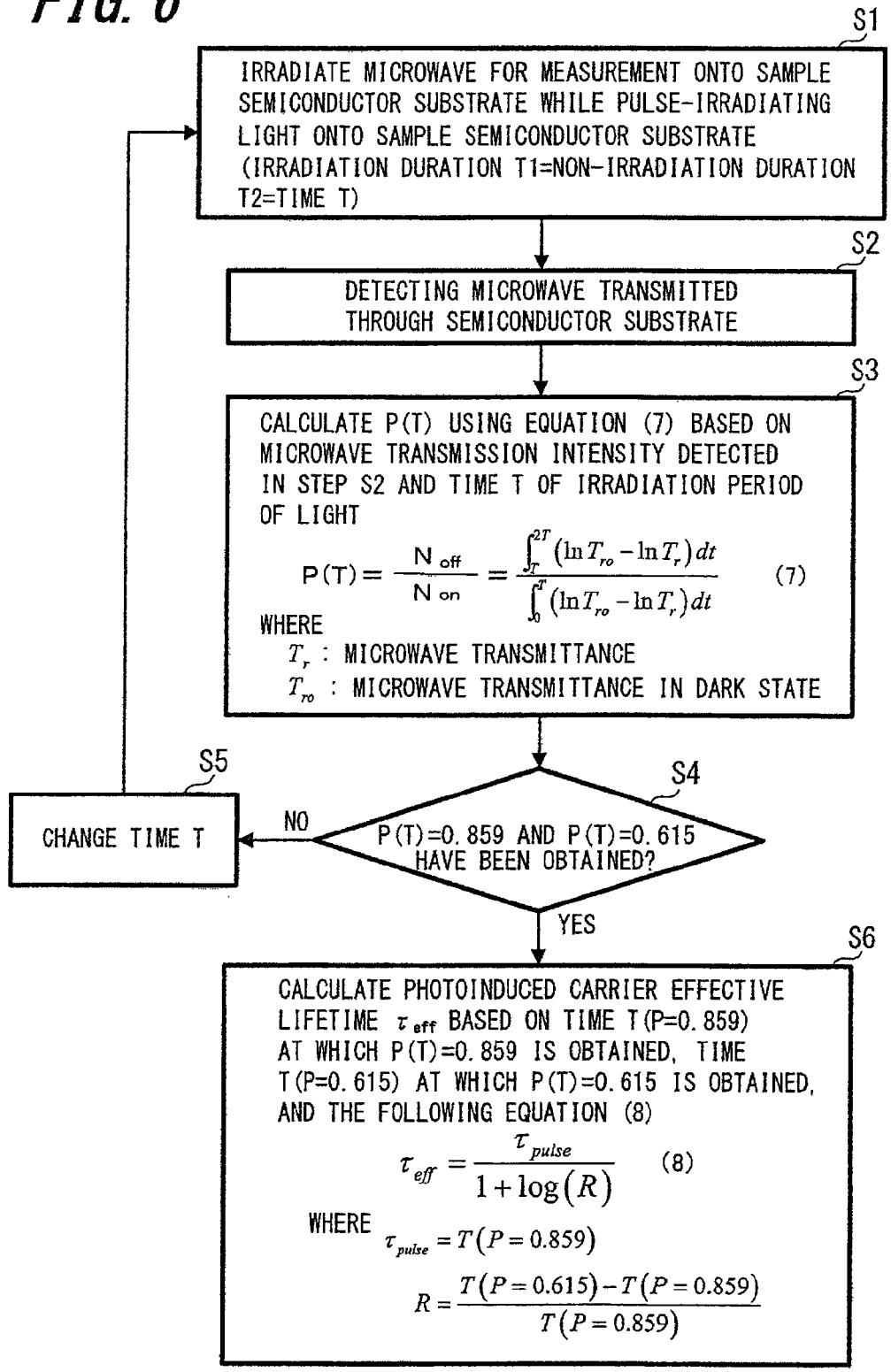
FIG. 6 is a flowchart for explaining a fourth embodiment of the present invention.

Next, a second example of the photoinduced carrier lifetime measuring method will be described below. The photoinduced carrier effective lifetime measuring method and the light incidence efficiency measuring method performed by using the photoinduced carrier lifetime measuring device shown in FIG. 1 or FIG. 2 will be described below with reference to a flowchart shown in FIG. 6.

First, the sample semiconductor substrate 1 OA is inserted into the gap 16A of the waveguide 15A of the photoinduced carrier lifetime measuring device shown in FIG. 1 or FIG. 2. At this time, the light-guiding plate 18 is disposed so as to abut the irradiation surface of the light of the semiconductor substrate 1 OA, or the semiconductor substrate 10A is disposed so that the irradiation surface of the light of the semiconductor substrate 1 OA faces the diffusion reflection plate 18'. Further, the reference semiconductor substrate 10B is inserted into the gap 16B of the waveguide 15B. It is preferred that the semiconductor substrates 1 OA, 10B are disposed so that they have the same direction with respect to the microwave source 11.

In such a state, in step S1, the light is periodically pulse-irradiated from the light source 12 onto the sample semiconductor substrate 10A. At the same time, the microwave for measurement is irradiated from the microwave source 11 onto the sample semiconductor substrate 10A and the reference semiconductor substrate 10B.

Figure 7A:
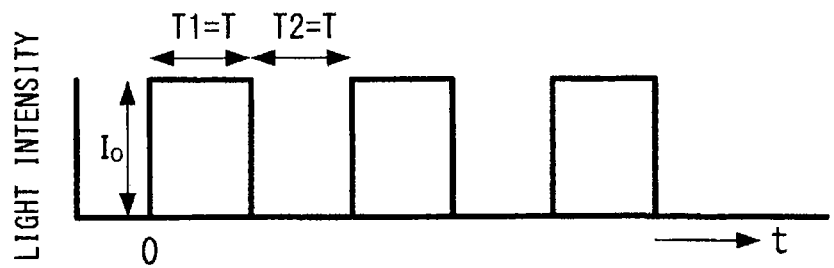

As shown in FIG. 7A, the pulse irradiation of the light is performed at an intensity of $I_0$ and at a period of irradiation duration T1/non-irradiation duration T2. At this time, the condition of the pulse irradiation is set to a predetermined time T, wherein irradiation duration T1=non-irradiation duration T2=time T. The irradiation duration T1 and the non-irradiation duration T2 can be set in a range from 0.01 ms to 0.1 s as the third embodiment, and preferably can be set in a range from 0.01 ms to 10 ms.

Figure 7B:
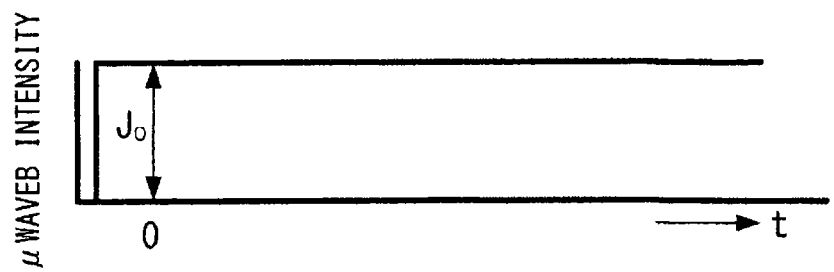

As shown in FIG. 7B, the irradiation of the microwave is continuously performed both during the irradiation duration T1 and during the non-irradiation duration T2 at an intensity of $J_0$. Here, a microwave having a frequency of 9.35 GHZ is used, for example.

Next, in step S2, the microwave irradiated onto the semiconductor substrates 10A, 10B and transmitted through the semiconductor substrates 10A, 10B in step S1 is detected by the detecting sections 13A, 13B. Here, as described before, detected and amplified microwave transmission intensity J can be obtained by detecting the microwave by the detecting sections 13A, 13B.

Next, in step S3, in the calculating section 14, based on the microwave transmission intensity J obtained in step S2 and the set irradiation duration T1=non-irradiation duration T2=time T, a carrier density ratio P(T) of the photoinduced carriers is calculated according to the following Equation (7). The carrier density ratio P(T) calculated here is the ratio of an average carrier density $N_{off}$ in the non-irradiation duration T2 (T→2T) to an average carrier density $N_{on}$ in the irradiation duration T1 (0→T).

[Mathematical expression 7]

$$P(T) = \frac{N_{off}}{N_{on}} = \frac{\int_T^{2T}(\ln T_{ro} - \ln T_r)\,dt}{\int_0^T(\ln T_{ro} - \ln T_r)\,dt} \quad (7)$$

where
Tr: microwave transmittance
Tr$_0$: microwave transmittance in dark state

In Equation (7), Tr is the microwave transmittance, and Tr$_0$ is the microwave transmittance in a dark state before the light is pulse-irradiated. The previously obtained microwave transmittance of the reference semiconductor substrate 10B, for example, may be used to calculate the microwave transmittances Tr, $Tr_0$. The microwave transmittance $Tr_0$ in the dark state is previously calculated before the measurement has been started in step S1.

Figure 7C:
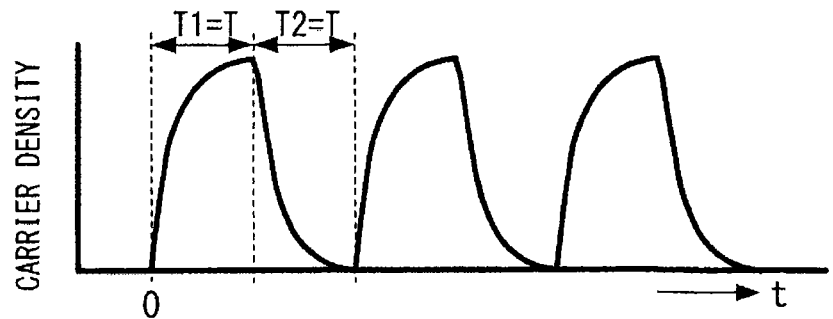

Incidentally, in the calculating section 14, the following judgment is performed before calculating the carrier density ratio P(T) by using the aforesaid Equation (7). In other words, two microwave transmission intensities respectively obtained in two sequential periods of the pulse irradiation of the light in step S2 are compared with each other. Further, it is judged, at a point where the difference of the two microwave transmission intensities compared has reached a predetermined value, that the change of the carrier density with time has become stable during the periodical pulse irradiation of the light, as shown in FIG. 7C. Thereafter, the calculation in step S3 is performed.

Next, in step S4, in the calculating section 14, it is judged whether P(T)=0.859 or P(T)=0.615 has been obtained as the carrier density ratio P(T) calculated in step S3. If both results of P(T)=0.859 and P(T)=0.615 are not obtained, the process will proceed to step S5; the process proceeds to step S6 only in the case where both results of P(T)=0.859 and P(T)=0.615 are obtained.

In step S5, the time T (=irradiation duration T1=non-irradiation duration T2) of the periodical pulse irradiation of the light in step S1 is changed. Here, in the calculating section 14, the result calculated in step S3 is fed back, and the time T is changed so that the carrier density ratio P(T) becomes close to P(T)=0.859 or P(T)=0.615.

Thereafter, in step S1, the light is periodically pulse-irradiated onto the sample semiconductor substrate 10A, and the measurement microwave is irradiated onto the semiconductor substrates 10A, 10B at a period of the time T changed in step S5. The pulse irradiation of the light and the irradiation of the microwave are performed by controlling the microwave source 11 and the light source 12 based on the time T changed in the calculating section 14. The control of microwave source 11 and the light source 12 is performed by the controller 19 connected to the calculating section 14.

Then the operation of step S1 to step S5 is repeatedly performed until it is judged that both results of P(T)=0.859 and P(T)=0.615 have been obtained in step S4.

On the other hand, if it is judged that both results of P(T)=0.859 and P(T)=0.615 have been obtained in step S4, the photoinduced carrier effective lifetime $\tau_{eff}$ will be calculated in step S6 by using the following Equation (8). However, T(P=0.859) is the time T at which P(T)=0.859 is reached. Further, T(P=0.615) is the time T at which P(T)=0.615 is reached. Incidentally, Equation (8) will be described later in more detail.

[Mathematical expression 8]

$$\tau_{eff} = \frac{\tau_{pulse}}{1 + \log(R)} \quad (8)$$

where $$\tau_{pulse} = T(P = 0.859)$$

$$R = \frac{T(P = 0.615) - T(P = 0.859)}{T(P = 0.859)}$$

As described in the below Example 3, it is confirmed that the effective lifetime $\tau_{eff}$ obtained by the photoinduced carrier lifetime measuring method according to the aforesaid fourth embodiment has good consistent with photoinduced carrier lifetime when continuously performing light irradiation.

In the photoinduced carrier lifetime measuring method according to the aforesaid fourth embodiment, the photoinduced carrier effective lifetime $\tau_{eff}$ is obtained without using the surface reflectivity r of the sample semiconductor substrate as a parameter. Further, since the light is periodically pulse-irradiated onto the sample semiconductor substrate, a measurement result with high sensitivity can be obtained by obtaining an integrated value of the microwave intensity detected for each of plural periodical pulse irradiations.

Thus, similar to the method of the third embodiment, it is possible to obtain the photoinduced carrier effective lifetime with high sensitivity even in the case where it is difficult to measure the surface reflectivity of the semiconductor substrate (for example, in the case of a solar cell structure that has a texture whose reflectivity actually can not be determined).

Incidentally, in the photoinduced carrier lifetime measuring method according to the aforesaid fourth embodiment, the carrier density ratio P(T) obtained in step S2 is fed back, and the time T is changed so that the carrier density ratio P(T) becomes close to P(T)=0.859 or P(T)=0.615. However, the photoinduced carrier lifetime measuring method according to the fourth embodiment is not limited to such steps, but the time T may also be sequentially changed within a predetermined ranged. In such a case, P(T)=0.859 and P(T)=0.615 are found from the carrier density ratios P(T) obtained by irradiating light at sequentially changed times T, so that T(P=0.859) and T(P=0.615) corresponding to P(T)=0.859 and P(T)=0.615 are obtained.

<About Equation (8)>

Equation (8) used in the fourth embodiment is derives as below.

If depth is x, time is t, and carrier volume density of the semiconductor substrate is n(x, t), then carrier density N(t) per unit area of a semiconductor substrate having thickness d can be calculated by the following Equation (9).

[Mathematical Expression 9]

$$N(t) = \int_0^d n(x,t) dx \quad (9)$$

Further, the carrier density ratio P(T) of the photoinduced carrier defined as Equation (7) can be expressed as the following Equation (10) by using the carrier density N(t) per unit area in Equation (9). Incidentally, the carrier density ratio P(T) is the ratio of the average carrier density $N_{off}$ in the non-irradiation duration T2 (T→2T) to the average carrier density $N_{on}$ in the irradiation duration T1 (0→T).

[Mathematical expression 10]

$$P(T) = \frac{N_{off}}{N_{on}} = \frac{\frac{1}{T}\int_T^{2T} N(t) dt}{\frac{1}{T}\int_0^T N(t) dt} \quad (10)$$

where $N_{off}$: average carrier surface density (surface density of the entire substrate at a depth of d) in dark state $N_{on}$: average carrier surface density (surface density of the entire substrate at a depth of d) under light irradiation T: irradiation duration per pulse of light (i.e., pulse width)

Here, if the defect of the sample semiconductor substrate is bulk defect only, the surface recombination velocity on the irradiation side of the light will be $S_{top}=0$, and the surface recombination velocity on the side of the rear surface opposite to the irradiation side of the light will be $S_{rear}=0$. In such a case, the carrier density $N_{on}$ in the irradiation duration T1

(0→T) and the average carrier density $N_{off}$ in the non-irradiation duration T2 (T→2T) are respectively expressed as the following Equations (11) and (12) using bulk lifetime $\tau_b$ of the minority carriers.

[Mathematical expression 11]

$$N(t) = F\tau_b\left(1 - e^{-\frac{t}{\tau_b}}\right) + F\tau_b \frac{e^{-\frac{T}{\tau_b}}}{1 + e^{-\frac{T}{\tau_b}}} e^{-\frac{t}{\tau_b}} \quad (O \to T) \quad (11)$$

$$N(t) = F\tau_b \frac{e^{\frac{T}{\tau_b}}}{1 + e^{-\frac{T}{\tau_b}}} e^{-\frac{t}{\tau_b}} \quad (T \to 2T) \quad (12)$$

where
$\tau_b$: bulk lifetime of minority carriers
F: carrier production rate

The following Equation (13) can be obtained by rewriting Equation (10) based on Equations (12) and (13).

[Mathematical expression 12]

$$P(T) = \frac{N_{off}}{N_{on}} = \frac{\frac{\tau_b}{T}\left(1 - e^{-\frac{T}{\tau_b}}\right)}{1 + e^{-\frac{T}{\tau_b}} - \frac{\tau_b}{T}\left(1 - e^{-\frac{T}{\tau_b}}\right)} \quad (13)$$

If T=$\tau_b$, and T=2$\tau_b$ in Equation (13), then Equation (13) becomes the following Equations (14) and (15).

[Mathematical Expression 13]

$$P(\tau_b) = \frac{e - 1}{2} \sim 0.859 \quad (14)$$

$$P(2\tau_b) = \frac{1 - e^{-2}}{1 + 3e^{-2}} \sim 0.615 \quad (15)$$

If the value expressed in Equation (14) is used to express the irradiation duration T1 (i.e., the pulse width) when the carrier density ratio P(T) is 0.859 as $\tau_{pulse}$, then $\tau_{pulse}$ can be expressed as the following Equation (16).

[Mathematical Expression 14]

$$\tau_{pulse} = T(P=0.859) \quad (16)$$

Further, R is defined as the following Equation (17). P(0.615) is the irradiation duration T1 when P(T)=0.615. T=P(0.859) is the irradiation duration T1 when P(T)=0.859.

[Mathematical Expression 15]

$$R = \frac{T(P=0.615) - T(P=0.859)}{T(P=0.859)} \quad (17)$$

The aforesaid Equation (8) is expressed by using the $\tau_{pulse}$ and R defined as above.

<Light Incidence Efficiency Measuring Method>

The light incidence efficiency measuring method for obtaining the effective light incidence efficiency of the semiconductor substrate based on the photoinduced carrier effective lifetime obtained by the measuring method described in the fourth embodiment is performed in the same manner as described in the third embodiment.

Example 3

Measurement of Photoinduced Carrier Lifetime

The photoinduced carrier effective lifetime of the semiconductor substrate was obtained by using the aforesaid photoinduced carrier lifetime measuring device and applying the photoinduced carrier lifetime measuring method according to the fourth embodiment.

In Example 3, the carrier density ratio P(T) with respect to the irradiation duration T1=non-irradiation duration T2=time T of the light was calculated using Equation (7) for each of plural silicon substrates (as semiconductor substrates) having different defect distributions. For each silicon substrate, the value of the bulk lifetime $\tau_b$ of the minority carriers (i.e., the photoinduced carriers), the value of the surface recombination velocity on the irradiation side of light $S_{top}$, and the value of the surface recombination velocity on the side of the rear surface opposite to the irradiation side of the light $S_{rear}$ were set to respective values. These values indicate the number of the defects in each portion (i.e., the bulk, the surface onto which light is irradiated, and the surface opposite to surface onto which light is irradiated) of the semiconductor substrate.

Figure 8:
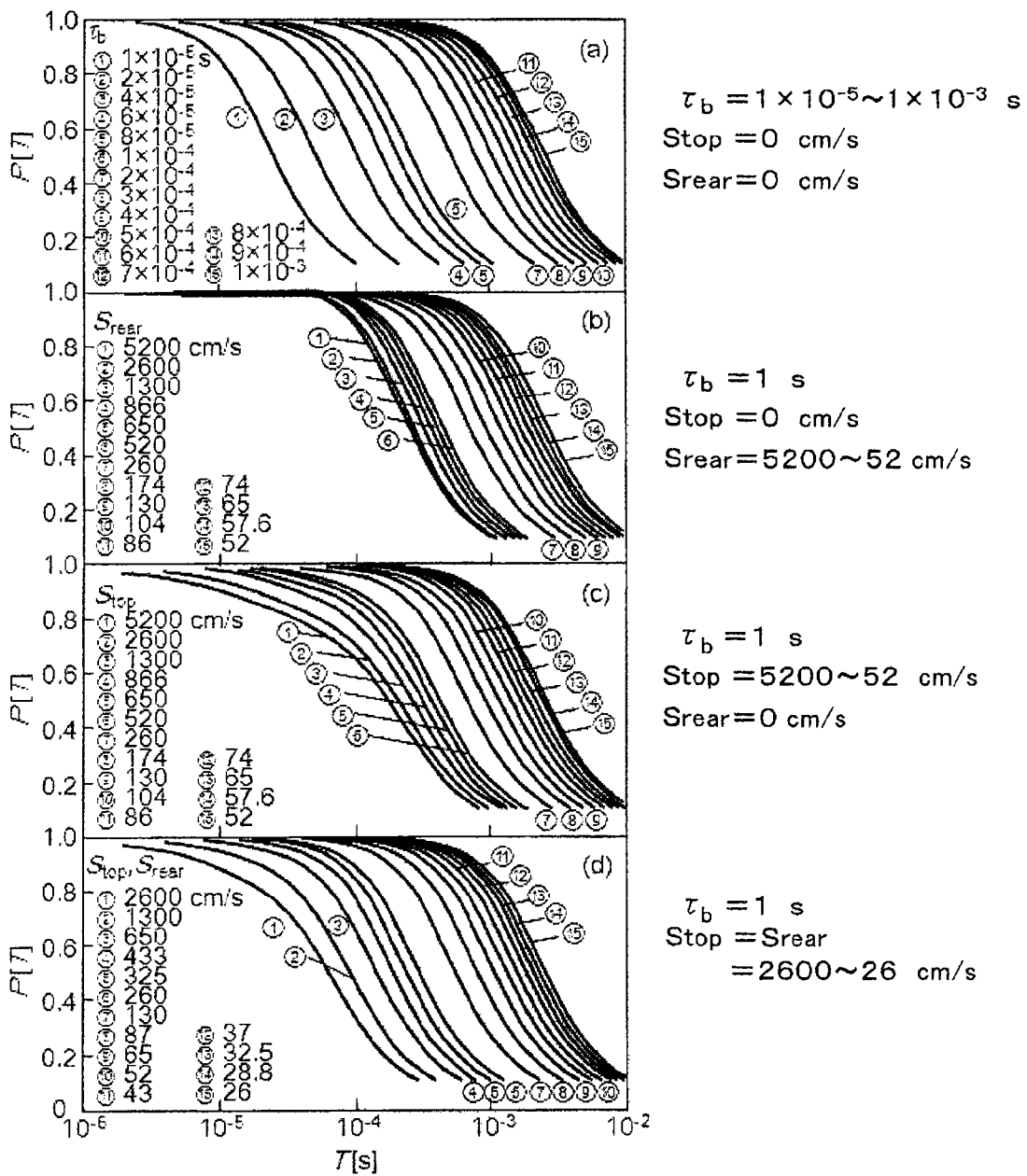
FIG. 8 shows carrier density ratio P(T) with respect to time T in the case where the minority carriers of a silicon substrate are holes.
Figure 9:
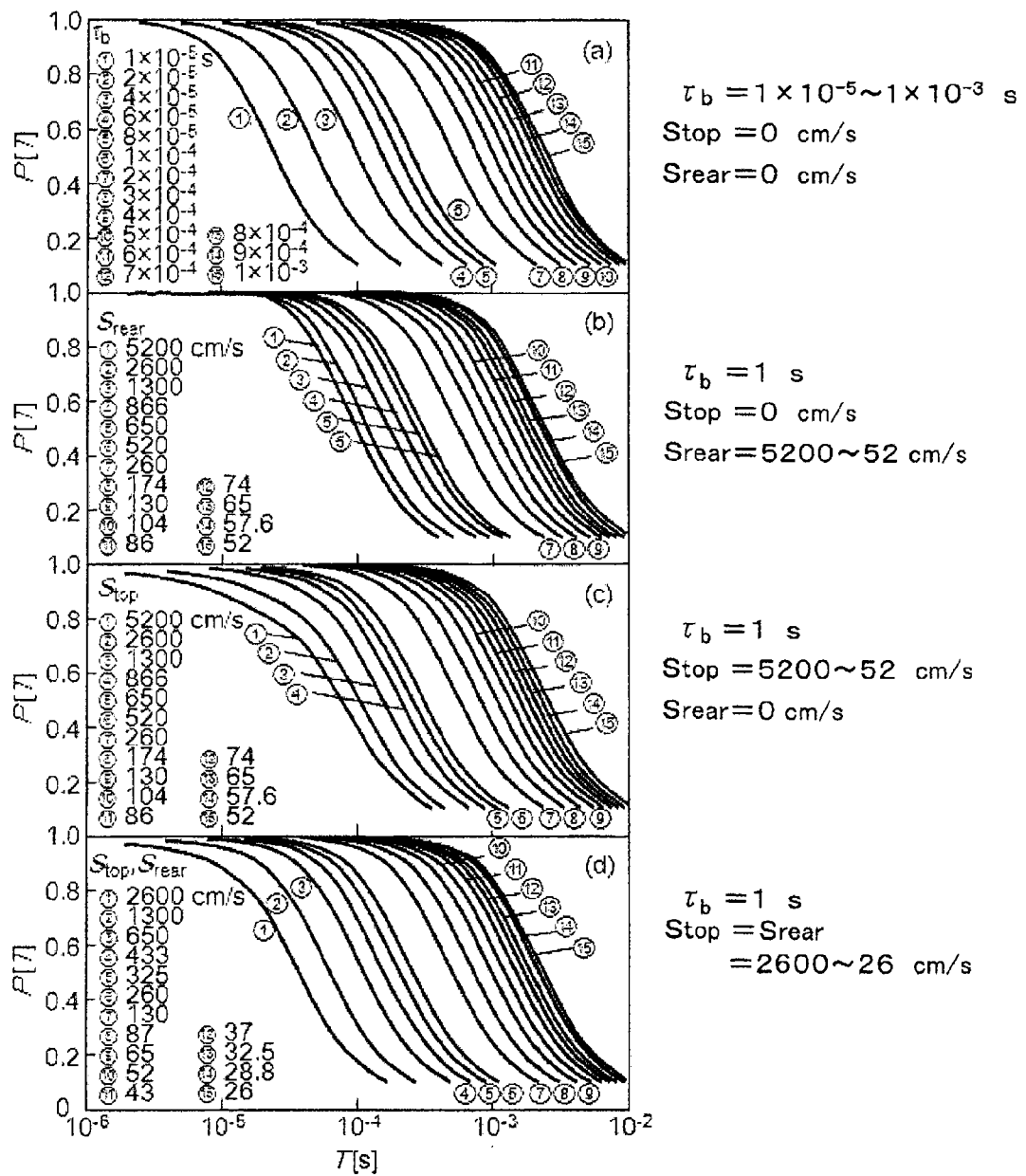
FIG. 9 shows carrier density ratio P(T) with respect to time T in the case where the minority carriers of the silicon substrate are electrons.

FIG. 8 shows the carrier density ratio P(T) with respect to the time T in the case where the minority carriers of the silicon substrate are holes. FIG. 9 shows the carrier density ratio P(T) with respect to the time T in the case where the minority carriers of the silicon substrate are electrons.

Figure 10:
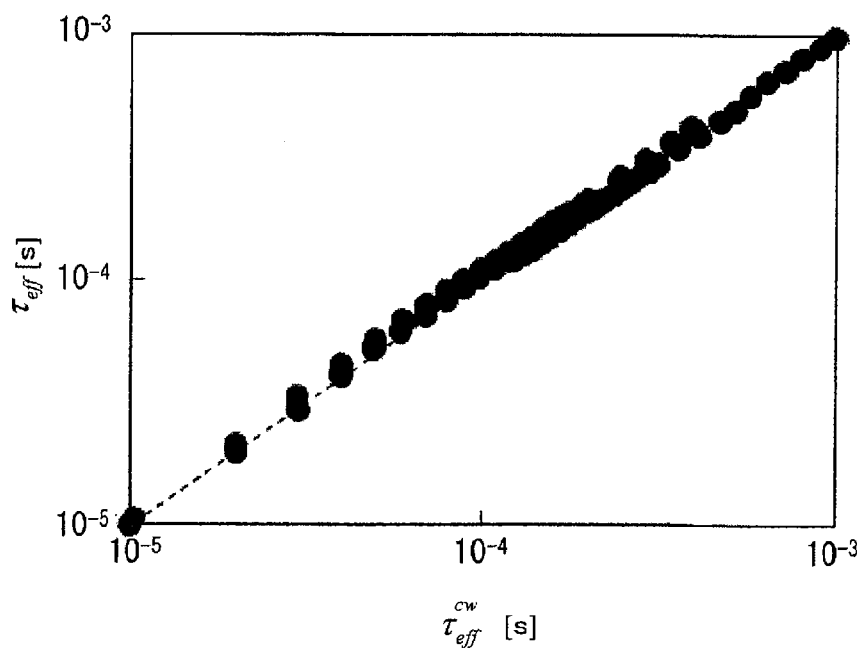
FIG. 10 is a graph showing the relation between the effective lifetime $\tau_{eff}$ calculated using Equation (8) and photoinduced carrier lifetime when continuously performing light irradiation obtained using Equation (18)

Next, the effective lifetime $\tau_{eff}$ was calculated for each silicon substrate having the aforesaid defect distribution by analyzing time T-carrier density ratio P(T) shown in FIGS. 8 and 9 and using Equation (8) shown in the fourth embodiment. FIG. 10 shows the relation between the effective lifetime $\tau_{eff}$ calculated using Equation (8) and the photoinduced carrier lifetime when continuously performing light irradiation obtained by the following Equation (18).

[Mathematical expression 16]

$$\tau_{eff}^{CW} = \tau_b \frac{\sqrt{\frac{D}{\tau_b}}\left(1 - \exp\left(-\frac{d}{\sqrt{D\tau_b}}\right)\right)}{\left(\sqrt{\frac{D}{\tau_b}} + S_{rear} + \left(\sqrt{\frac{D}{\tau_b}} - S_{rear}\right)\exp\left(-\frac{d}{\sqrt{D\tau_b}}\right)\right)} \\ \cdot \frac{\left(\sqrt{\frac{D}{\tau_b}} + S_{rear} + \left(\sqrt{\frac{D}{\tau_b}} - S_{rear}\right)\exp\left(-\frac{d}{\sqrt{D\tau_b}}\right)\right)}{\left(\sqrt{\frac{D}{\tau_b}} + S_{rear}\right)\left(\sqrt{\frac{D}{\tau_b}} + S_{top}\right) - \left(\sqrt{\frac{D}{\tau_b}} - S_{top}\right)\left(\sqrt{\frac{D}{\tau_b}} - S_{rear}\right)\exp\left(-\frac{2d}{\sqrt{D\tau_b}}\right)} \quad (18)$$

$\tau_{eff}^{CW}$: photoinduced carrier lifetime when continuously performing light irradiation
D: diffusion coefficient of minority carriers
$\tau_b$: bulk lifetime of minority carriers
$S_{top}$: surface recombination velocity on irradiation side of induction light
$S_{rear}$: surface recombination velocity on side of rear surface opposite to irradiation side of induction light
d: thickness of substrate As shown in FIG. 10, the effective lifetime calculated using Equation (8) of the fourth embodiment is in consistency with the photoinduced carrier lifetime when continuously performing light irradiation shown as Equation (18). Thus, it is confirmed that the photoinduced carrier effective lifetime $\tau_{eff}$ of the semiconductor substrate can be obtained with high accuracy.

Incidentally, in the fourth embodiment, the ratio of the average carrier density $N_{off}$ in the non-irradiation duration T2 (T→2T) to the average carrier density $N_{on}$ in the irradiation duration T1 (0→T) is used as the carrier density ratio P(T). However, the carrier density ratio P(T) is not such limited, but may also be, for example, the ratio of the average carrier density $N_{off}$ in the non-irradiation duration T2 (T→2T) to the carrier density $n_0$ when continuously performing light irradiation. In such a case, other suitable value is used as the T(P) that constitutes the R of Equation (8).

5. Fifth Embodiment

Next, a third example of the photoinduced carrier lifetime measuring method will be described below. Here, a method for measuring surface distribution of the photoinduced carrier effective lifetime of the semiconductor substrate will be described below by using the photoinduced carrier lifetime measuring device shown in FIG. 1 or FIG. 2.

First, the sample semiconductor substrate 10A on the microwave irradiation surface side is divided into a plurality of areas. Here, the sample semiconductor substrate 10A on the microwave irradiation surface side is divided into a plurality of areas, where the size of each area is 1 cm×0.5 cm, for example.

Next, the photoinduced carrier lifetime measuring method according to the aforesaid third embodiment or the fourth embodiment is performed on each of the divided areas, and the photoinduced carrier effective lifetime of each area is measured. In such a case, the semiconductor substrate 10A is moved in a direction perpendicular to the incident direction of the microwave by a movable stage arranged in the photoinduced carrier lifetime measuring device to thereby selectively irradiate microwave onto each area of the semiconductor substrate 10A to perform measurement; or the irradiation position of the microwave is moved by a microwave scanning section arranged in the photoinduced carrier lifetime measuring device to thereby selectively irradiate microwave onto each area of the semiconductor substrate 10A to perform measurement.

It is possible to obtain the surface distribution of the photoinduced carrier effective lifetime by the photoinduced carrier lifetime measuring method according to the fifth embodiment. It is possible to measure the surface distribution with high spatial resolution by using a microwave having relatively high frequency.

<Light Incidence Efficiency Measuring Method>

The light incidence efficiency measuring method for obtaining the effective light incidence efficiency of the semiconductor substrate based on the photoinduced carrier effective lifetime obtained by the measuring method described in the fifth embodiment is performed in the same manner as described in the third embodiment.

Example 4

Measurement of Photoinduced Carrier Lifetime

Figure 11:
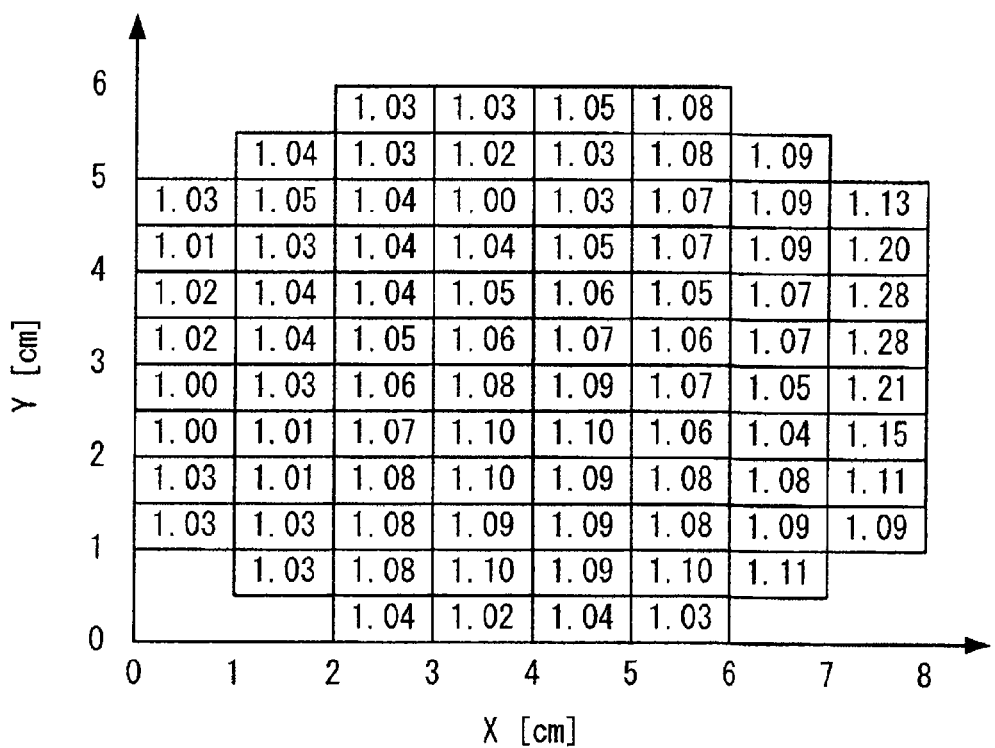
FIG. 11 is a table showing distribution of the effective lifetime $\tau_{eff}$ calculated for each area of the semiconductor substrate.

FIG. 11 shows a distribution of the effective lifetime $\tau_{eff}$ calculated for each area of the semiconductor substrate. A microwave having a frequency of 9.35 GHZ was used to perform the measurement. Thus, it was confirmed that the photoinduced carrier lifetime could be measured with a spatial resolution of about 1 cm.

The measuring device and measuring method for detecting the microwave transmitted through the semiconductor substrate have been described in the aforesaid first embodiment to fifth embodiment; however, the present invention also includes a measuring device and measuring method for detecting the microwave reflected by the semiconductor substrate.

In such a case, as for the photoinduced carrier lifetime measuring device, in the configuration shown in FIG. 1 or FIG. 2, the detecting sections 13A, 13B may be disposed in the position where the waveguide 15, on which the microwave source 11 is mounted, is branched into two waveguides. Further, as for the photoinduced carrier lifetime measuring method, the microwave transmission intensity may be substituted with microwave reflection intensity.

Further, the aforesaid embodiments and examples are described base on a case where the irradiation duration T1 is equal to the non-irradiation duration T2; however, in the present invention, T1 and T2 do not have to be equal to each other, but may also be suitably set respectively.

It is to be understood that the present invention is not limited to the embodiments described above, and various modifications and variations can be made without departing from the spirit and scope of the present invention.

EXPLANATION OF REFERENCE NUMERALS

10A semiconductor substrate (sample)
10B semiconductor substrate (reference)
11 microwave source
12 light source
13A, 13B detecting section
14 calculating section
15, 15A, 15B waveguide
16A, 16B gap
17 optical fiber
18 light-guiding plate
18' diffusion reflection plate
19 controller

The invention claimed is:

1. A photoinduced carrier lifetime measuring method comprising:
    irradiating, by a microwave source, a microwave onto a semiconductor substrate while periodically pulse-irradiating, by an irradiating light source, a light onto the semiconductor substrate;
    detecting, by a detector, the microwave transmitted through the semiconductor substrate or reflected by the semiconductor substrate; and
    obtaining, by calculating circuitry, the effective lifetime of photoinduced carriers generated in the semiconductor substrate by the pulse irradiation of the light, based on an irradiation duration T1 and a non-irradiation duration T2 when pulse-irradiating the light and an integrated value of each microwave intensity obtained by the detection;
    wherein the light pulse irradiation is performed plural times, each with a changed irradiation duration T1 and a changed non-irradiation duration T2,
    the measuring method further comprising:
    detecting, by the detector, the microwave for each of the plural times of pulse irradiation; and
    obtaining, by the calculating circuitry, the effective lifetime of the photoinduced carriers generated in the semiconductor substrate by the light, based on each irradiation duration T1 and non-irradiation duration T2 and an integrated value of each microwave intensity obtained by each detection;

wherein the detection of the microwave is performed in the non-irradiation duration T2 separated from the irradiation duration T1; and wherein the effective lifetime of the photoinduced carriers generated in the semiconductor substrate by the light is obtained based on the relation between the irradiation duration T1 and non-irradiation duration T2 and the ratio of a photoinduced carrier density corresponding to the integrated value of the microwave intensity detected in the non-irradiation duration T2 to a photoinduced carrier density in a period that includes at least the irradiation duration T1.

2. The photoinduced carrier lifetime measuring method according to claim 1, wherein the light pulse irradiation is performed with a plurality of different periods where the irradiation duration T1=the non-irradiation duration T2, the measuring method further comprising the steps of:

calculating, by the calculating circuitry, the ratio P(T) of a photoinduced carrier density <n> obtained based on the integrated value of the microwave intensity detected in the non-irradiation duration T2 to a photoinduced carrier density obtained based on the microwave intensity detected in the irradiation duration T1;

identifying, by the calculating circuitry, the irradiation duration T1 (=the non-irradiation duration T2) respectively at P(T)=0.859 and P(T)=0.615; and calculating, by the calculating circuitry, effective lifetime $\tau_{\text{eff}}$ using the following Equation (8)

$$\tau_{\text{eff}} = \frac{\tau_{\text{pulse}}}{1 + \log(R)} \quad (8)$$

where $$\tau_{\text{pulse}} = T(P = 0.859)$$

$$R = \frac{T(P = 0.615) - T(P = 0.859)}{T(P = 0.859)}.$$

3. The photoinduced carrier lifetime measuring method according to claim 1, further comprising:

previously preparing, by the calculating circuitry, a data table obtained by plotting a photoinduced carrier density ratio with respect to the irradiation duration T1 (=non-irradiation duration T2) for each of a plurality of effective lifetimes, each of the effective lifetimes having a different value;

pulse-irradiating, by the irradiating light source, the light onto a sample semiconductor substrate;

calculating, by the calculating circuitry, the photoinduced carrier density ratio based on the integrated value of the microwave intensity detected for the sample semiconductor substrate; and obtaining, by the calculating circuitry, the effective lifetime of the photoinduced carriers in the sample semiconductor substrate by fitting the irradiation duration T1 (=non-irradiation duration T2) used in the detection and the photoinduced carrier density ratio obtained by the calculation to the data table.

4. The photoinduced carrier lifetime measuring method according to claim 1, further comprising:

dividing a principal surface of the semiconductor substrate into a plurality of areas, and individually irradiating the microwave onto each area to thereby individually obtain the effective lifetime of the photoinduced carriers for each area.

5. The photoinduced carrier lifetime measuring method according to claim 1, wherein the irradiation duration T1 and the non-irradiation duration T2 of the light are changed in a range from 0.01 ms to 10 ms.

6. The photoinduced carrier lifetime measuring method according to claim 1, wherein the wavelength of the light ranges from 250 nm to 2500 nm.

7. A light incidence efficiency measuring method comprising:

irradiating, by a microwave source, a microwave onto a semiconductor substrate while periodically pulse-irradiating, by an irradiating light source, a light onto the semiconductor substrate;

detecting the microwave transmitted through the semiconductor substrate or reflected by the semiconductor substrate;

obtaining the effective lifetime of photoinduced carriers generated in the semiconductor substrate by the pulse irradiation of the light, based on an irradiation duration T1 and a non-irradiation duration T2 when pulse-irradiating the light and an integrated value of each microwave intensity obtained by the detection;

wherein the light pulse irradiation is performed plural times, each with a changed irradiation duration T1 and a changed non-irradiation duration T2, detecting the microwave for each of the plural times of pulse irradiation;

obtaining, by a calculating circuitry, the effective lifetime of the photoinduced carriers generated in the semiconductor substrate by the light, based on each irradiation duration T1 and non-irradiation duration T2 and an integrated value of each microwave intensity obtained by each detection;

wherein the detection of the microwave is performed in the non-irradiation duration T2 separated from the irradiation duration T1; and obtaining light incidence efficiency (1−r) from the following:

$$n=(1-r)G\tau_{\text{eff}}$$

where r is surface reflectivity, n is carrier density of photoinduced carriers, G is light intensity (energy of one photon), and $\tau_{\text{eff}}$ is the obtained effective lifetime of photoinduced carriers;

wherein the carrier density is obtained based on an integrated value of the microwave intensity detected in the non-irradiation duration T2.

8. A photoinduced carrier lifetime measuring device comprising:

a light source adapted to pulse-irradiate a light for generating photoinduced carriers in a sample;

a microwave source adapted to generate a microwave for being irradiated onto the sample;

a detector adapted to detect the microwave transmitted through the sample or reflected by the sample; and calculating circuitry configured to calculate the effective lifetime of the photoinduced carriers generated in the sample by the pulse irradiation of the light based on an irradiation duration T1 and a non-irradiation duration T2 when periodically pulse-irradiating the light for a plurality of times and an integrated value of the intensity of the microwave detected by the detector;

wherein the light source is further adapted to perform the light pulse irradiation plural times, each with a changed irradiation duration T1 and a changed non-irradiation duration T2, the detector is further adapted to detect the microwave for each of the plural times of pulse irradiation;

the calculating circuitry is further configured to obtain the effective lifetime of the photoinduced carriers generated in the semiconductor substrate by the light, based on each irradiation duration T1 and non-irradiation duration T2 and an integrated value of each microwave intensity obtained by each detection;

the detector is further adapted to perform the detection of the microwave in the non-irradiation duration T2 separated from the irradiation duration T1; and the calculating circuitry is further configured to obtain the effective lifetime of the photoinduced carriers generated in the semiconductor substrate by the light based on the relation between the irradiation duration T1 and non-irradiation duration T2 and the ratio of a photoinduced carrier density corresponding to the integrated value of the microwave intensity detected in the non-irradiation duration T2 to a photoinduced carrier density in a period that includes at least the irradiation duration T1.

9. The photoinduced carrier lifetime measuring device according to claim 8, wherein the light source irradiates the light with a plurality of different periods where irradiation duration T1=non-irradiation duration T2.

10. The photoinduced carrier lifetime measuring device according to claim 8, further comprising:

a position aligning section for selectively irradiating the microwave generated by the microwave source onto each of a plurality of areas of the sample, wherein the plurality of areas are obtained by dividing a principal surface of the sample.

11. A light incidence efficiency measuring device comprising:

a light source adapted to pulse-irradiate a light for generating photoinduced carriers in a sample;

a microwave source adapted to generate a microwave for being irradiated onto the sample;

a detector adapted to detect the microwave transmitted through the sample or reflected by the sample; and calculating circuitry configured to calculate the effective lifetime of the photoinduced carriers generated in the sample by the pulse irradiation of the light based on an irradiation duration T1 and a non-irradiation duration T2 when periodically pulse-irradiating the light for a plurality of times and an integrated value of the intensity of the microwave detected by the detector, and calculate light incidence efficiency (1−r) based on the effective lifetime from the following:

$$n=(1-r)G\tau_{\mathit{eff}}$$

where r is surface reflectivity, n is carrier density of photoinduced carriers, G is light intensity (energy of one photon), and $\tau_{\mathit{eff}}$ is the obtained effective lifetime of photoinduced carriers;

wherein the calculating circuitry is configured to obtain the carrier density based on an integrated value of the microwave intensity detected in the non-irradiation duration T2;

wherein the light source is further adapted to perform the light pulse irradiation plural times, each with a changed irradiation duration T1 and a changed non-irradiation duration T2, the detector is further adapted to detect the microwave for each of the plural times of pulse irradiation;

the calculating circuitry is further configured to obtain the effective lifetime of the photoinduced carriers generated in the semiconductor substrate by the light, based on each irradiation duration T1 and non-irradiation duration T2 and an integrated value of each microwave intensity obtained by each detection;

the detector is further adapted to perform the detection of the microwave in the non-irradiation duration T2 separated from the irradiation duration T1; and the calculating circuitry is further configured to obtain the effective lifetime of the photoinduced carriers generated in the semiconductor substrate by the light based on the relation between the irradiation duration T1 and non-irradiation duration T2 and the ratio of a photoinduced carrier density corresponding to the integrated value of the microwave intensity detected in the non-irradiation duration T2 to a photoinduced carrier density in a period that includes at least the irradiation duration T1.

* * * * *